United States Patent
Cai et al.

(10) Patent No.: US 10,183,941 B2
(45) Date of Patent: Jan. 22, 2019

(54) PYRIMIDINE OR PYRIDOPYRIDONE COMPOUND AND APPLICATION THEREOF

(71) Applicant: GUANGZHOU BEBETTER MEDICINE TECHNOLOGY CO., LTD., Guangdong (CN)

(72) Inventors: Xiong Cai, Guangdong (CN); Changgeng Qian, Guangdong (CN); Junqi Li, Guangdong (CN); Yuanhui Qing, Guangdong (CN); Yanyan Wang, Guangdong (CN); Weicai Xue, Guangdong (CN); Huajin You, Guangdong (CN)

(73) Assignee: GUANGZHOU BEBETTER MEDICINE TECHNOLOGY CO., LTD., Guangdong (CN)

( * ) Notice: Subject to any disclaimer, the term of this patent is extended or adjusted under 35 U.S.C. 154(b) by 0 days.

(21) Appl. No.: 15/764,884

(22) PCT Filed: May 31, 2016

(86) PCT No.: PCT/CN2016/084056
§ 371 (c)(1),
(2) Date: Mar. 30, 2018

(87) PCT Pub. No.: WO2017/054484
PCT Pub. Date: Apr. 6, 2017

(65) Prior Publication Data
US 2018/0297995 A1    Oct. 18, 2018

(30) Foreign Application Priority Data
Sep. 30, 2015    (CN) .......................... 2015 1 0646418

(51) Int. Cl.
*C07D 471/04*    (2006.01)
*A61P 35/00*    (2006.01)

(52) U.S. Cl.
CPC ............ *C07D 471/04* (2013.01); *A61P 35/00* (2018.01)

(58) Field of Classification Search
None
See application file for complete search history.

(56) References Cited

FOREIGN PATENT DOCUMENTS

| CN | 101374840 | 2/2009 |
|---|---|---|
| CN | 103288824 | 9/2013 |

(Continued)

OTHER PUBLICATIONS

"International Search Report (Form PCT/ISA/210)", dated Aug. 24, 2016, with English translation thereof, pp. 1-4.

*Primary Examiner* — Karl J Puttlitz
(74) *Attorney, Agent, or Firm* — JCIPRNET

(57) ABSTRACT

The present invention discloses a pyrimidine or pyridopyridone compound as shown in formula (I) and an application thereof relating to the technical field of medicament preparation. The compound can selectively suppress cyclin-dependent kinases (Cdks) CDK4 and CDK6 with almost no suppression of the activity of the kinase CDK2. Thus, the compound can be used for various diseases caused by cell cycle control disorders involving CDK4 and CDK6, and particularly in the treatment of malignant tumors.

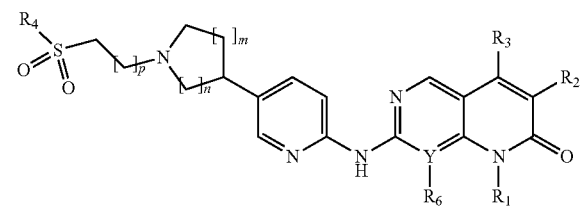

12 Claims, 4 Drawing Sheets

(56) References Cited

FOREIGN PATENT DOCUMENTS

CN    104812756    *  7/2015
WO    2014183520   *  11/2014

* cited by examiner

PYRIMIDINE OR PYRIDOPYRIDONE COMPOUND AND APPLICATION THEREOF

CROSS-REFERENCE TO RELATED APPLICATION

This application is a 371 of international application of PCT application serial no. PCT/CN2016/084056, filed on May 31, 2016, which claims the priority benefit of China application no. 201510646418.4, filed on Sep. 30, 2015. The entirety of each of the above-mentioned patent applications is hereby incorporated by reference herein and made a part of this specification.

BACKGROUND

1. Field of the Invention

The present disclosure relates to the technical field of pharmaceutical preparation, particularly to a pyrimidine or pyridopyridone compound and an application thereof.

2. Description of Related Art

Cyclin-dependent kinase (CDK) and cyclin are important factors in cell cycle control. CDK can bind to cyclin to form heterodimers, wherein CDK is a catalytic subunit, and cyclin is a regulatory subunit, and form various cyclin-CDK complexes, thus phosphorylating different substrates and playing a part in promoting and transforming the different phases of cell cycle.

There are at least nine CDKs in mammals. The transformation of cells from G1 to S phase is mainly controlled by G1 CDK kinase. CDK kinases that bind to G1 cyclin mainly include CDK2, CDK4 and CDK6. Cyclin D mainly binds to CDK4 and CDK6 and regulates the activity of the latter; cyclin E binds to CDK2 in G1/S phase, exhibiting CDK2 kinase activity and promoting the cells entry into S phase. G2/M phase are controlled mainly by CDK1 kinase, and cyclin A, cyclin B bind to CDK1, and CDK1 phosphorylates substrate protein, such as, histone H1 phosphorylation will lead to chromosome condensation, and lamin phosphorylation will lead to the disintegration of nuclear membrane. In M phase, M phase-promoting factor (MPF) activates the anaphase-promoting complex (APC), linking ubiquitin to cycli A and cyclin B, allowing them to be degraded by proteasome by the ubiquitination and completing a cell cycle (Malumbres M. et al. Nat Cell Biol 11:1275, 2009; Malumbres M. et al. Nat Rev Cancer 9:153, 2009).

Cell cycle disorder is a common feature of human tumors. Tumor cells typically undergo unconventional proliferation, genomic instability (increased DNA mutations and chromosomal aberrations), and chromosomal instability (increase in the number of chromosomes). The cell cycle is regulated by CDKs family kinases. Tumor cells have aberrant CDKs activity due to changes in CDKs per se or their modulators or mitogenic upstream pathways related genes and table genetic genes (Cicenas J. J. Cancer Res ClinOncol 147: 1409, 2011; Rizzolio F. et al. Curr Drug Targets 11:279, 2010).

Over the past decade, the development of CDK inhibitors as a new anti-tumor drug has become a hot spot in the global pharmaceutical industry. More than 20 CDK inhibitors have been put into clinical development. Although anti-tumor preclinical pharnacodynamic results of CDK inhibitors are significant, most of the earlier clinical trial results were unsatisfactory. The main problems include the lack of efficacy and higher toxicity in solid tumors. (Guha M. Nat Rev Drug Dis 11:892, 2012). The clinical study was terminated due to the efficacy and toxicity of CDK inhibitors AG-24322, ZK-304709, SNS-032, R547, Seliciclib, and AZD5438. However, after the analysis of the causes of serious side effects, it is found that these drugs lacked selectivity for the inhibition of CDK subtypes and thereby produced serious side effects.

Recent studies have shown that CDK1 is involved in the normal cell cycle control. In the case of other CDKs being inhibited, CDK1 activity is retained sufficient to maintain the normal cell cycle. The toxic side effects of CDK inhibitors are related to the inhibition of CDK1 and CDK2. In contrast, CDK4 and CDK6 subtypes are not necessary for the mammalian cell cycle, and they only play an important role in the proliferation of specific cell types, and become key targets for tumor inhibition (Guha M. Nat Rev Drug Dis 11:892, 2012).

CDK4 and CDK6 are two closely related kinases which bind to Cyclin D in the tumor cell cycle and drive the G1 phase into S phase, which are essential for the cell cycle progression of DNA replication and cell division. In more than 90% of human tumors, it is found that the transition control mechanism of G1-S phase is altered through various genes and biochemical adaptations. P16 and human retinoblastoma (Rb) inhibitor proteins are important tumor inhibitor proteins which can control the cell cycle. P16 gene protein inhibits the feedback loops of CDK4, CyclinD1 and Rb, and prevents over proliferation of cell to achieve the purpose of inhibiting tumor by regulating the protein activity of Rb. It has been demonstrated that activation of CDK4 and CDK6 in human tumors (such as breast cancer and myeloma) results in changes in cell cycle. The inhibition of CDK4 and CDK6 can prevent the inactivation of the tumor inhibitor protein Rb and interfere with the progression of tumor cell cycle (Choi Y J and Anders L, Oncogene 33: 1890-903, 2014).

Recent studies have also found that CDK6 induces the expressions of the tumor inhibitor gene $p16^{INK4a}$ and the angiogenesis factor VEGF-A as a part of a transcription complex. CDK6 can exert a promoting effect for tumor by enhancing cell proliferation and angiogenesis stimulation (Kollmann K. et al. Cancer Cell 24:167, 2013).

Palbociclib (PD-0332991) can selectively inhibit CDK4 and CDK6 and restore the cell cycle control, and thereby block tumor cell proliferation. Pfizer corporation filed a petition for NDA with the U.S. Food and Drug Administration (FDA) in May of this year based on their interim clinical trial results. According to the phase II study by Pfizer, in the postmenopausal women patients with locally advanced or metastatic breast cancer with estrogen receptor positive (ER$^+$) and human epidermal growth factor receptor 2 negative (HER$_2^-$), compared with the treatment group of standard therapeutic drug letrozole, the progression-free survival (PFS) of disease in the combination group of palbociclib and letrozole was significantly prolonged statistically (20.2 months vs. 10.2 months, p=0.0004), reaching the primary end point of the research. Unlike non-selective CDK inhibitors, CDK4/6 inhibitor PD-0332991 has fewer side effects which mainly include leukocyte reduction and fatigue (Pfizer Press Release 2014.4.6). In phannacokinetics, the blood exposure of oral absorption of palbociclib is low. Clinical results of Phase I showed that the blood concentration was 10-91 mg/ml and AUC was 58-641 ng h/ml after a single oral dose of 25-150 mg. Since the elimination half-life is long (Average 25.9 hours), repeated daily dosing will lead to drug accumulation (Keith T, et al. Clin Cancer Res 18:568, 2011).

Selective CDK4 and CDK6 inhibitors Palbociclib, LY2835219 and LEE011 enter phase III clinical trials for the treatment of advanced breast cancer. Since CDK4/6 plays a key role in the cell cycle control disorders of various solid tumors and hematological tumors. At present, the clinical evaluation of these drugs further includes metastatic breast cancer, liposarcoma, non-small cell lung cancer, liver cancer, ovarian cancer, glioblastoma, melanoma, multiple myeloma and lymphoma and the like.

SUMMARY

Based on this, the purpose of the present disclosure is to provide a pyrimidine or pyridopyridone compound to overcome the drawbacks that CDK inhibitors are lack of selectivity in the prior art. The compound can selectively suppress cyclin-dependent kinases (Cdks) CDK4 and CDK6 with almost no suppression activity on kinase CDK2. Thus, the compound can be used in various diseases caused by cell cycle control disorders involving CDK4 and CDK6, particularly in the treatment of malignant tumors.

Pyrimidine or pyridopyridone compounds or their pharmaceutical acceptable salts or stereoisomers as shown in formula (I):

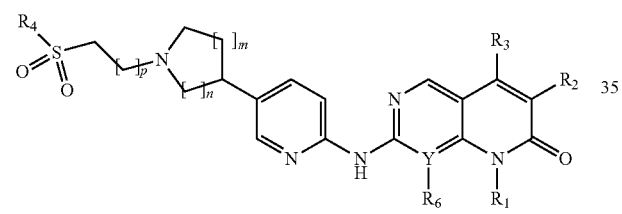

Wherein: Y is selected from the group consisting of C and N, and no substitution by $R_6$ when Y is N;

$R_1$ is selected from the group consisting of C1-C6 alkyl, C3-C6 cycloalkyl and C3-C6 cycloalkyl-substituted methyl;

$R_2$ is selected from the group consisting of halogen, $COR_5$, and $COOR_5$;

$R_3$ is selected from the group consisting of H, C1-C6 alkyl;

$R_4$ is selected from the group consisting of C1-C6 alkyl, hydroxy-substituted C1-C6 alkyl, alkoxy-substituted C1-C6 alkyl, phenyl, and halogen-substituted phenyl;

$R_5$ is selected from the group consisting of H, C1-C6 alkyl, C1-C6 fluoroalkyl, and C3-C6 cycloalkyl;

$R_6$ is selected from the group consisting of H, F, CN, and $CH_3$;

m is selected from the group consisting of 0, 1 and 2;

n is selected from the group consisting of 1, 2 and 3; and p is selected from the group consisting of 1, 2 and 3.

In some embodiments, $R_4$ is selected from the group consisting of C1-C6 alkyl, hydroxy-substituted C1-C6 alkyl, and alkoxy-substituted C1-C6 alkyl, wherein hydroxy-substituted C1-C6 alkyl is preferably hydroxy-substituted ethyl.

In some embodiments, $R_4$ is selected from the group consisting of methyl, ethyl, propyl, and isopropyl. $R_4$ is preferably methyl.

In some embodiments, m is selected from: 1; n is selected from: 2; p is selected from: 1 or 2.

In some embodiments, Y is selected from: N.

In some embodiments, $R_1$ is selected from C3-C6 cycloalkyl; $R_2$ is selected from $COR_5$; $R_3$ is selected from C1-C6 alkyl; $R_5$ is selected from C1-C6 alkyl; and $R_6$ is selected from: H.

In some embodiments, $R_1$ is selected from cyclopentyl; $R_2$ is selected from $COR_5$; $R_3$ is selected from methyl; $R_5$ is selected from methyl and ethyl; $R_5$ is preferably methyl; $R_6$ is selected from: H.

In some embodiments, the following compounds are selected:

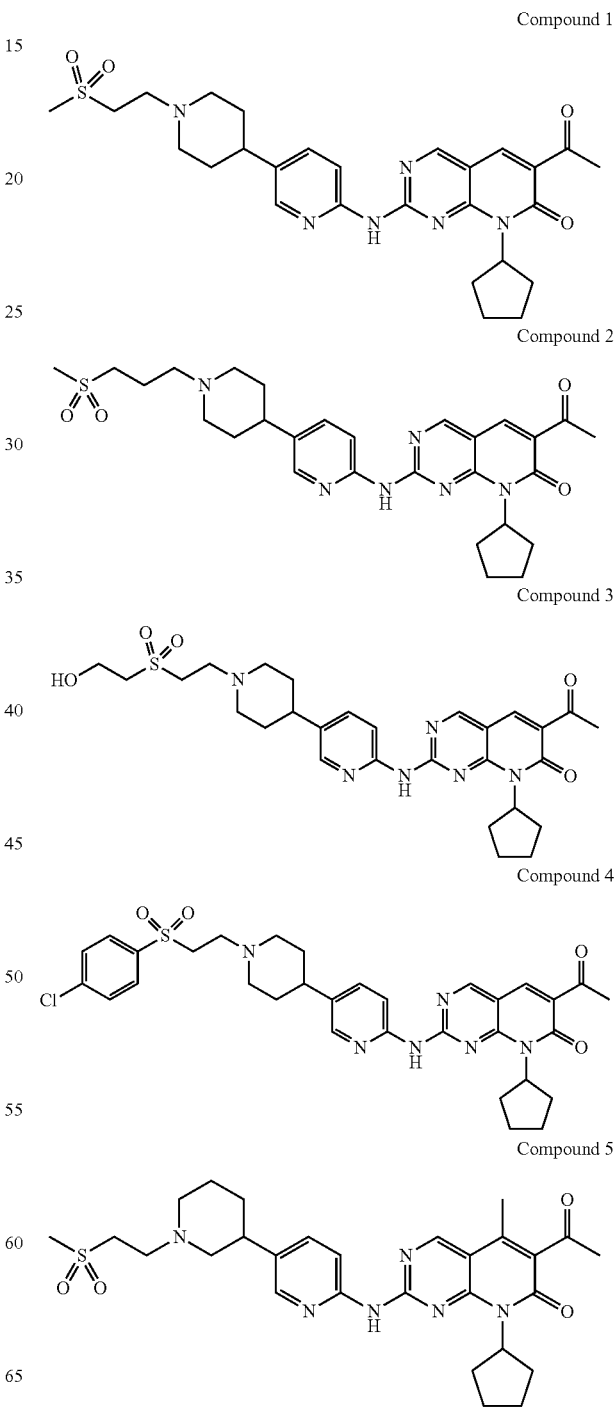

-continued

Compound 6

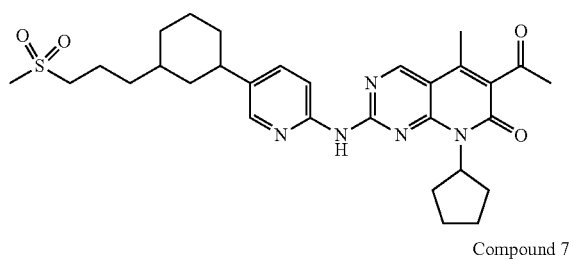

Compound 7

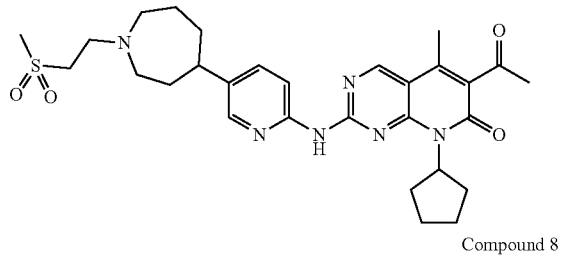

Compound 8

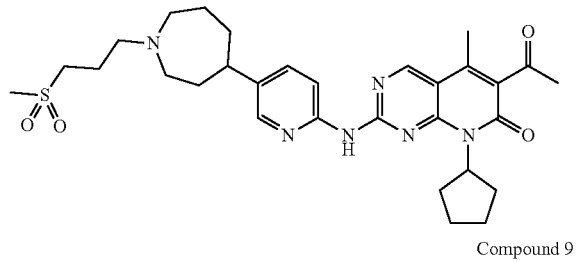

Compound 9

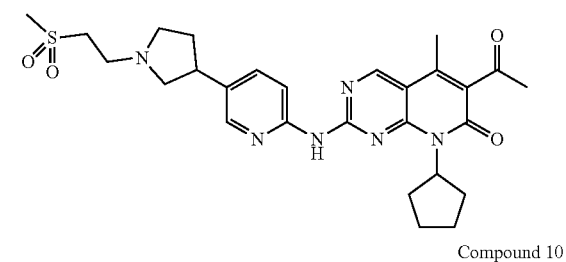

Compound 10

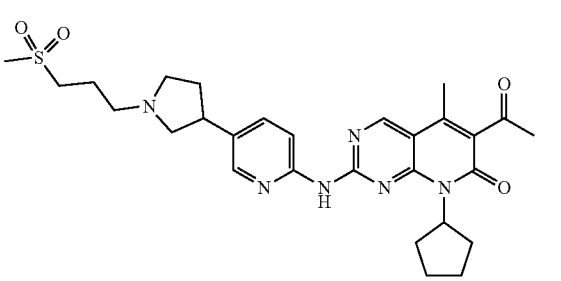

Compound 11

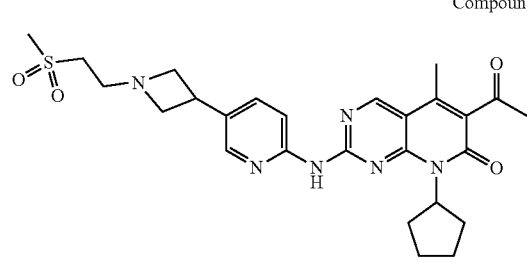

-continued

Compound 12

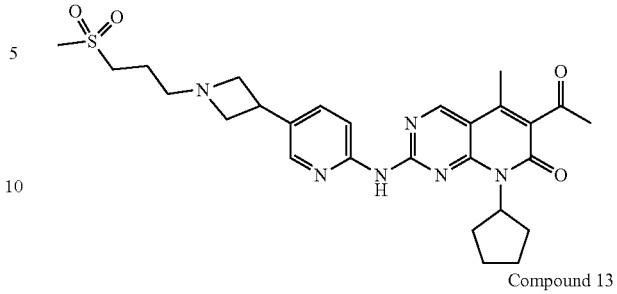

Compound 13

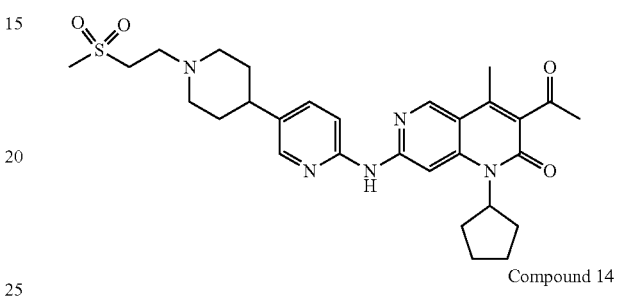

Compound 14

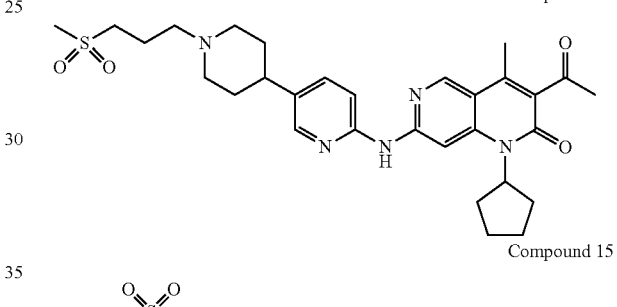

Compound 15

The disclosure further discloses the use of the pyrimidine or pyridopyridone compound or pharmaceutical acceptable salt or stereoisomer thereof in the preparation of antitumor drugs.

In some embodiments, the tumors are solid tumors and hematological tumors.

In some embodiments, the solid tumors and hematological tumors include breast cancer, liposarcoma, non-small cell lung cancer, liver cancer, ovarian cancer, glioblastoma, melanoma, multiple myeloma and mantle cell lymphoma.

In some embodiments, the breast cancer includes locally advanced or metastatic breast cancer with estrogen receptor positive and human epidermal growth factor receptor 2 negative in postmenopausal women.

The disclosure further discloses an antitumor dpyrimidineg composition, which comprises the pyrimidine or pyridopyridone compound or pharmaceutical acceptable salt or stereoisomer according to any one of claims 1 to 9 as an active ingredient, and a pharmaceutical acceptable carrier.

Compared with the prior art, the present disclosure has the following beneficial effects:

The pyrimidine or pyridopyridone compounds as shown in formula I of the present disclosure are a series of novel compounds which can selectively inhibit CDK4 and CDK6 and can be used in various diseases caused by cell cycle control disorders involving CDK4 and CDK6, and particularly in the treatment of malignant tumors.

In the present disclosure, the compounds have high activities of CDK6 and CDK4 when R4 is alkyl; and the compounds lose CDK6 activity when R4 is aryl.

In particular, some of these compounds have the characteristics of high selectivity, high activity and strong anti-proliferation effects on tumor cells. In the enzyme activity inhibition experiments, the IC$_{50}$ of inhibition on CDK4 and CDK6 can be lower than 10 nM (10 nmol/L), and the IC$_{50}$ of inhibition on CDK2 is greater than 500 nM with almost no inhibitory activity. In the experiment of tumor cell proliferation inhibition, the IC$_{50}$ of SW620, ZR-75-1 and MDA-MB-231 tumor cell lines can reach 0.5 μM or even lower than 0.1 μM. In the cell cycle inhibition experiment, G1 phase cell stopped growing and S phase cell decreased in a concentration-dependent manner, with the IC$_{50}$ of about 40 nM, slightly better than that of the positive control. In the Western Blot experiment, the phosphorylation of Rb at Ser780 sites could be effectively reduced after acting on MDA-MB-231 breast cancer cells.

In addition, some compounds showed very superior characteristics in the pharmacokinetic experiment. After administrating the same dose to the test animals, the AUC value of the compounds of the present disclosure was higher than that of the positive control, especially for Compound 2 therein, the AUC thereof is about 9 times that of the positive control, and has excellent oral absorption effect.

DESCRIPTION OF THE EMBODIMENTS

Figure 1:
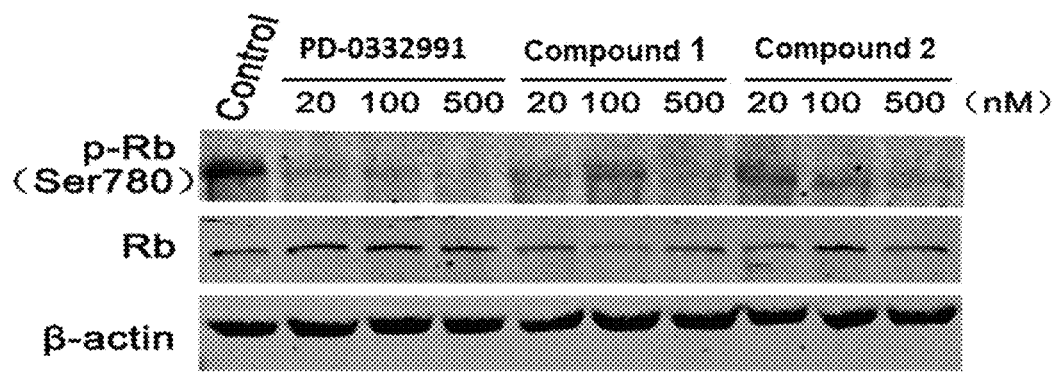
FIG. 1 is a schematic diagram showing that a CDK4/6 inhibitor prevents the phosphorylation of Rb of MDA-MB-231 breast cancer cells in Example 6.

In addition to the standard methods known in the documents or exemplified in the laboratory procedures, the compounds of the present disclosure can be prepared using the reactions shown in the following schemes. Accordingly, the following illustrative schemes are for the purpose of illustration and are not to be limited to the compounds listed or any particular substituents, the methods described are intended to describe, and not to limit the scope of the disclosure.

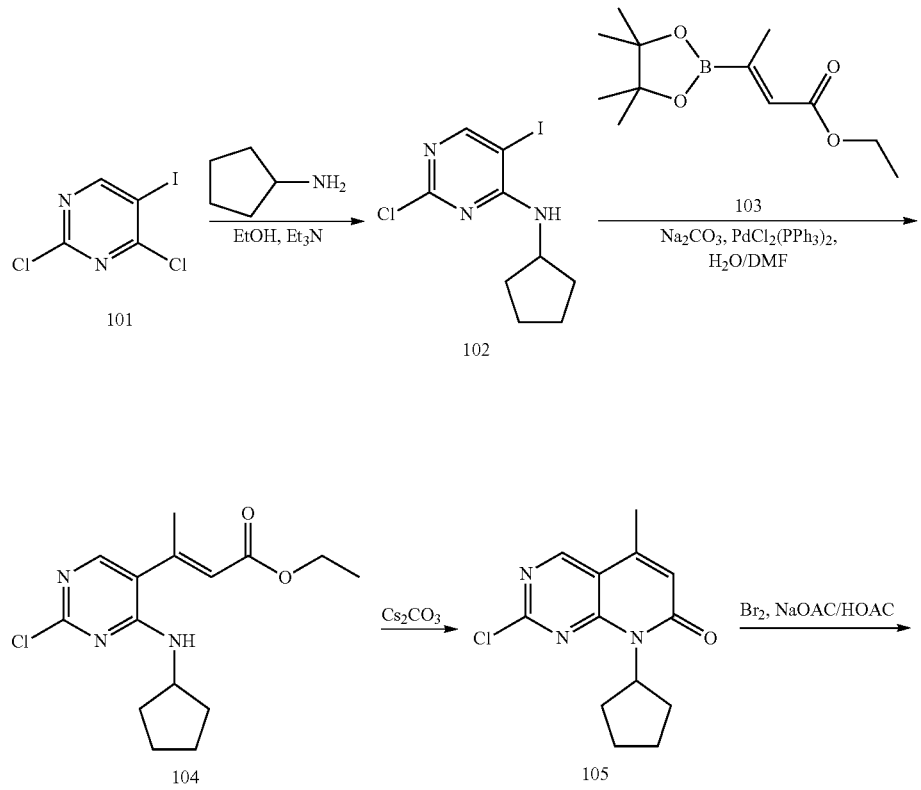

Scheme I

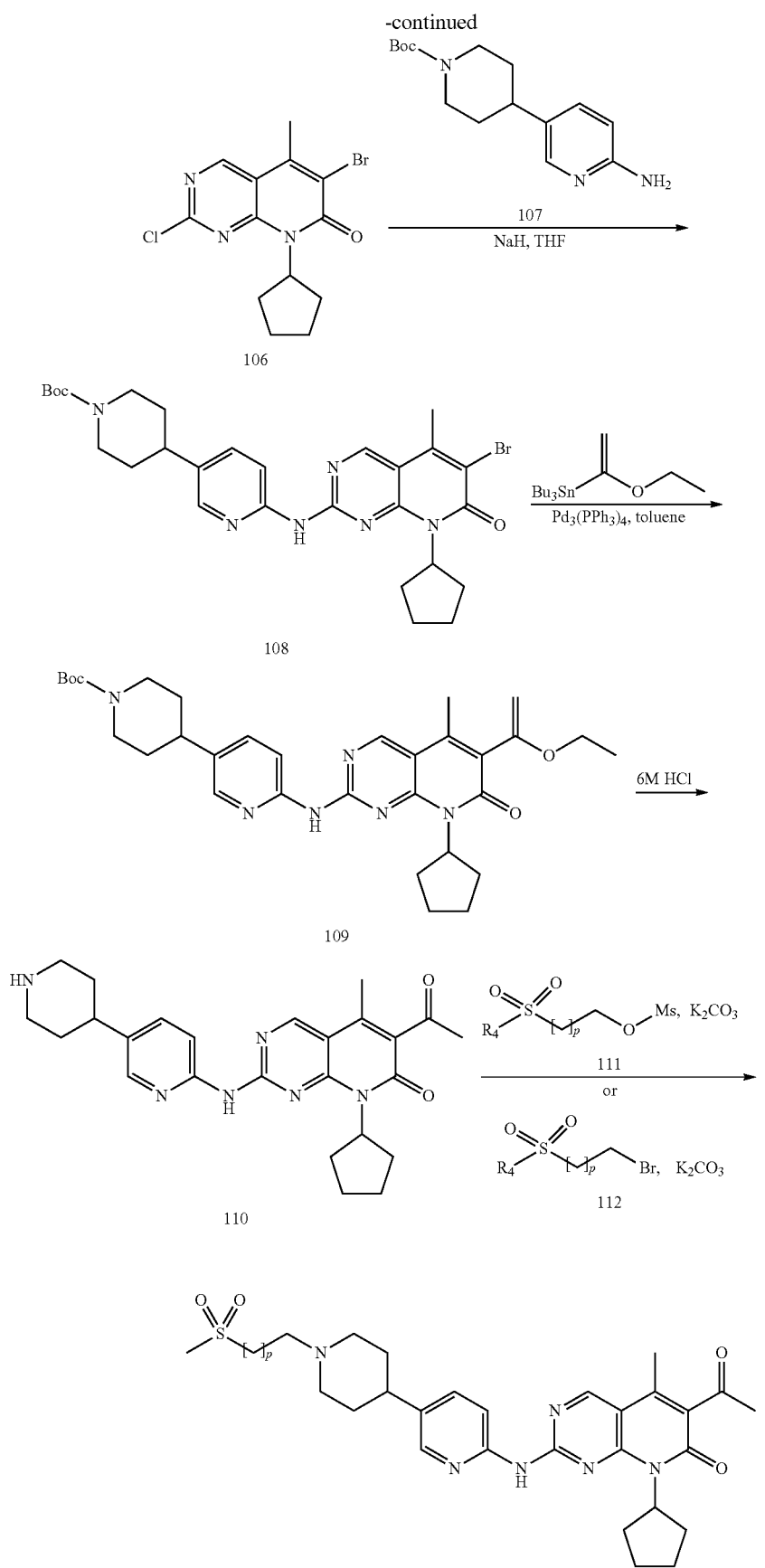

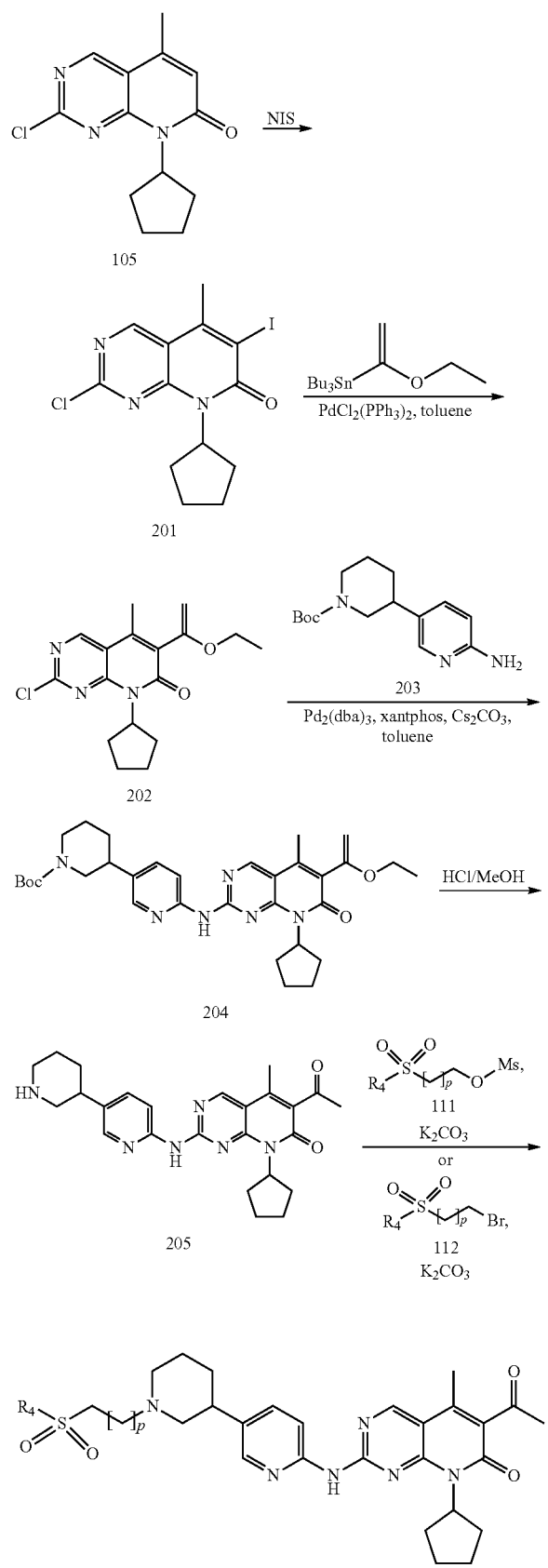
Scheme II
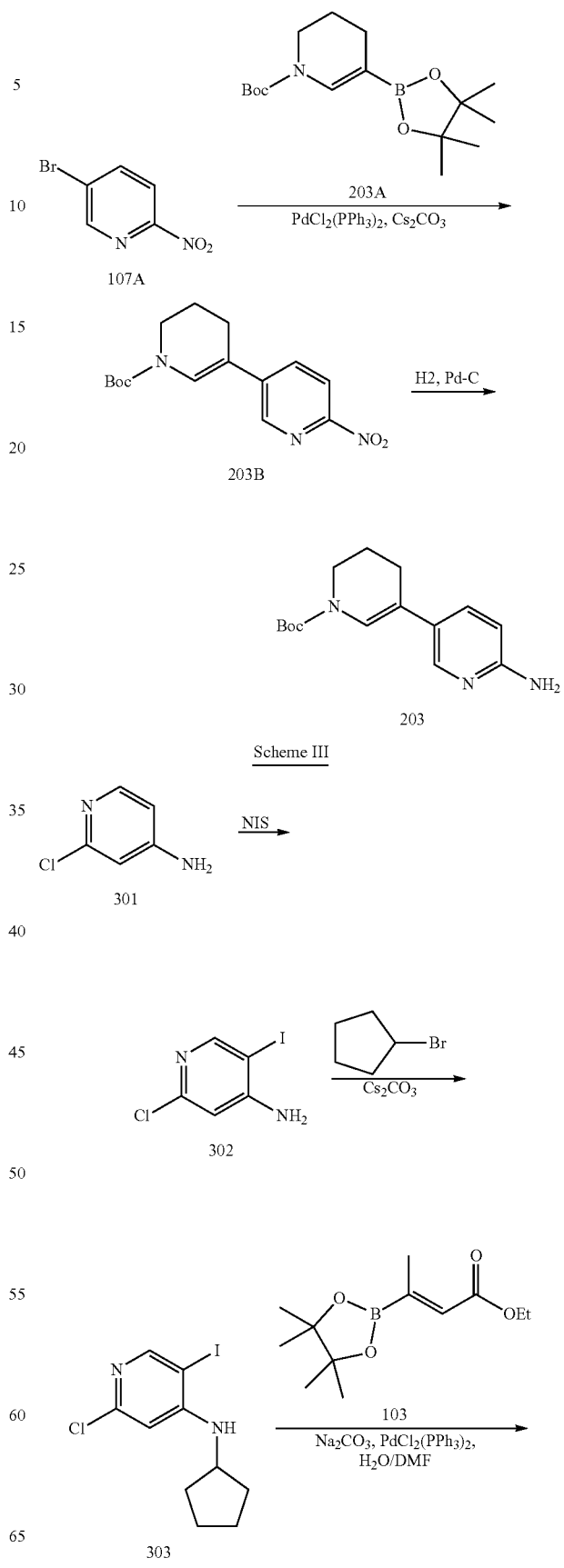
Scheme III

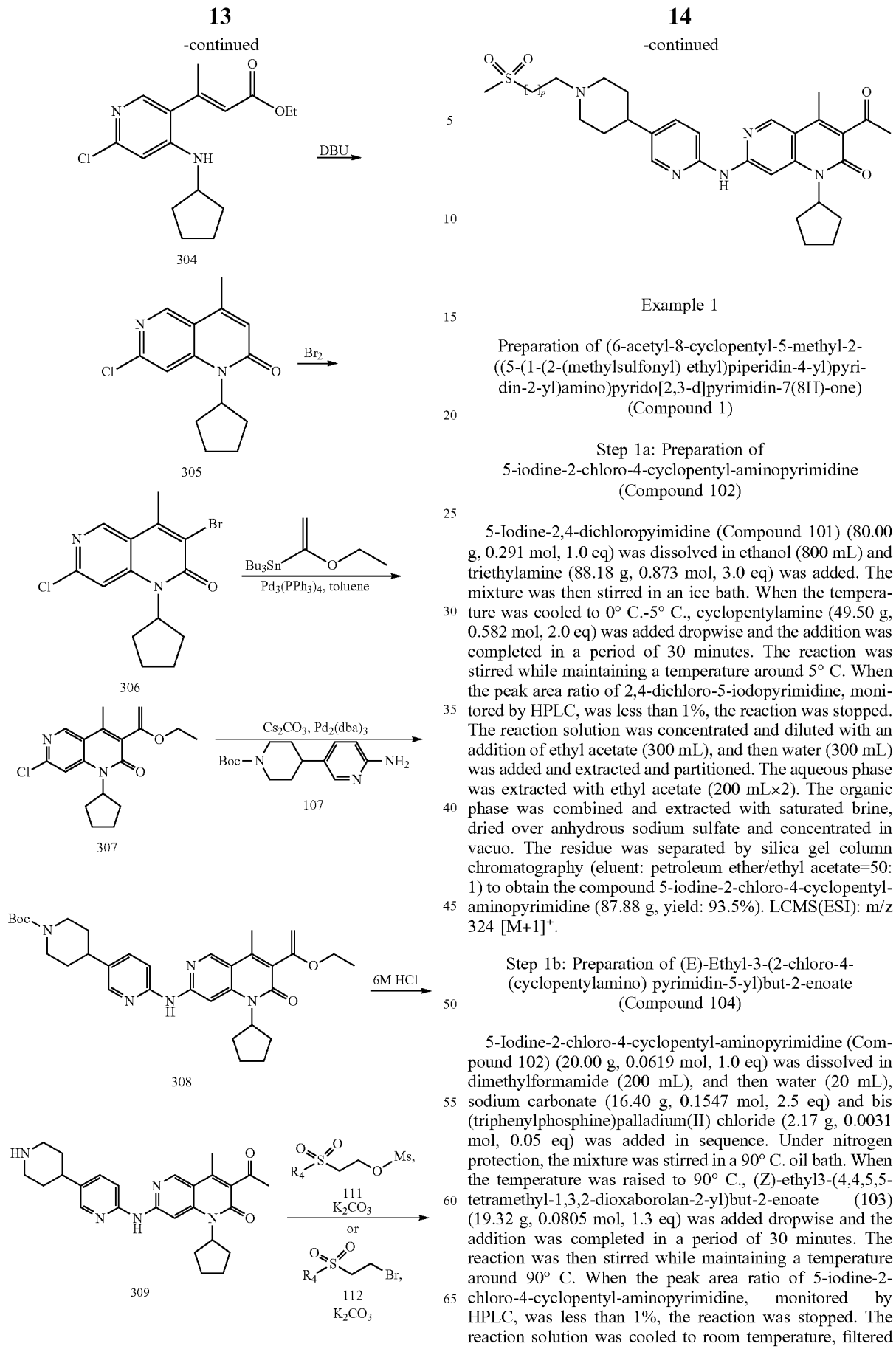

Example 1

Preparation of (6-acetyl-8-cyclopentyl-5-methyl-2-((5-(1-(2-(methylsulfonyl) ethyl)piperidin-4-yl)pyridin-2-yl)amino)pyrido[2,3-d]pyrimidin-7(8H)-one) (Compound 1)

Step 1a: Preparation of 5-iodine-2-chloro-4-cyclopentyl-aminopyrimidine (Compound 102)

5-Iodine-2,4-dichloropyimidine (Compound 101) (80.00 g, 0.291 mol, 1.0 eq) was dissolved in ethanol (800 mL) and triethylamine (88.18 g, 0.873 mol, 3.0 eq) was added. The mixture was then stirred in an ice bath. When the temperature was cooled to 0° C.-5° C., cyclopentylamine (49.50 g, 0.582 mol, 2.0 eq) was added dropwise and the addition was completed in a period of 30 minutes. The reaction was stirred while maintaining a temperature around 5° C. When the peak area ratio of 2,4-dichloro-5-iodopyrimidine, monitored by HPLC, was less than 1%, the reaction was stopped. The reaction solution was concentrated and diluted with an addition of ethyl acetate (300 mL), and then water (300 mL) was added and extracted and partitioned. The aqueous phase was extracted with ethyl acetate (200 mL×2). The organic phase was combined and extracted with saturated brine, dried over anhydrous sodium sulfate and concentrated in vacuo. The residue was separated by silica gel column chromatography (eluent: petroleum ether/ethyl acetate=50:1) to obtain the compound 5-iodine-2-chloro-4-cyclopentyl-aminopyrimidine (87.88 g, yield: 93.5%). LCMS(ESI): m/z 324 [M+1]$^+$.

Step 1b: Preparation of (E)-Ethyl-3-(2-chloro-4-(cyclopentylamino) pyrimidin-5-yl)but-2-enoate (Compound 104)

5-Iodine-2-chloro-4-cyclopentyl-aminopyrimidine (Compound 102) (20.00 g, 0.0619 mol, 1.0 eq) was dissolved in dimethylformamide (200 mL), and then water (20 mL), sodium carbonate (16.40 g, 0.1547 mol, 2.5 eq) and bis (triphenylphosphine)palladium(II) chloride (2.17 g, 0.0031 mol, 0.05 eq) was added in sequence. Under nitrogen protection, the mixture was stirred in a 90° C. oil bath. When the temperature was raised to 90° C., (Z)-ethyl3-(4,4,5,5-tetramethyl-1,3,2-dioxaborolan-2-yl)but-2-enoate (103) (19.32 g, 0.0805 mol, 1.3 eq) was added dropwise and the addition was completed in a period of 30 minutes. The reaction was then stirred while maintaining a temperature around 90° C. When the peak area ratio of 5-iodine-2-chloro-4-cyclopentyl-aminopyrimidine, monitored by HPLC, was less than 1%, the reaction was stopped. The reaction solution was cooled to room temperature, filtered and the filter cake was washed with methyl tert-butyl ether (100 mL). To the filtrate was added methyl tert-butyl ether (200 mL) and water (400 mL) and extracted and partitioned. The aqueous phase was extracted with methyl tert-butyl ether (200 mL×2). The organic phase was combined and washed with saturated brine (200 mL), dried over anhydrous sodium sulfate and concentrated in vacuo. The residue was separated by silica gel column chromatography (eluent: petroleum ether/ethyl acetate=20:1) to obtain the compound (E)-ethyl-3-(2-chloro-4-(cyclopentylamino)pyrimidin-5-yl) but-2-enoate (13.85 g, yield: 72.4%). LCMS (ESI): m/z 310 [M+1]$^+$.

Step 1c: Preparation of 2-chloro-8-cyclopentyl-5-methyl-8H-pyrido[2,3-d]pyrimidin-7-one (Compound 105)

Compound (E)-ethyl-3-(2-chloro-4-(cyclopentylamino) pyrimidin-5-yl) but-2-enoate (104) (20.00 g, 0.0647 mol, 1.0 eq) was dissolved in dimethylformamide (200 mL) and cesium carbonate (42.16 g, 0.1294 mol, 2.0 eq) was then added and stirred at room temperature. When the peak area ratio of Compound 104, monitored by HPLC, was less than 1%, the reaction was stopped. The reaction solution was filtered and the filter cake was washed with methyl tert-butyl ether (100 mL). To the filtrate was added methyl tert-butyl ether (200 mL) and water (400 mL) and extracted and partitioned. The aqueous phase was extracted with methyl tert-butyl ether (200 mL×2). The organic phase was combined and washed with saturated brine (200 mL), dried over anhydrous sodium sulfate and concentrated in vacuo. The residue was separated by silica gel column chromatography (eluent: petroleum ether/ethyl acetate=10:1) to obtain the compound 2-chloro-8-cyclopentyl-5-methyl-8H-pyrido[2,3-d]pyrimidin-7-one (13.94 g, yield: 81.9%). LCMS (ESI): m/z 264 [M+1]$^+$.

Step 1d: Preparation of 6-bromo-2-chloro-8-cyclopentyl-5-methyl-8H-pyrido[2,3-d]pyrimidin-7-one (Compound 106)

Compound 2-chloro-8-cyclopentyl-5-methyl-8H-pyrido [2,3-d]pyrimidin-7-one (105) (19.84 g, 0.0754 mol, 1.0 eq) was dissolved in acetic acid (200 mL) and sodium acetate (24.75 g, 0.3017 mol, 4.0 eq) was added and stirred at room temperature. Bromine (48.26 g, 0.3017 mol, 4.0 eq) was then added dropwise slowly and the addition was completed in a period of 20 minutes. The mixture was placed in a 50° C. oil bath and stirred. When the peak area ratio of Compound 105, monitored by HPLC, was less than 1%, the reaction was stopped. After the reaction solution was cooled to room temperature, saturated aqueous sodium sulfite solution (200 mL) and dichloromethane (300 mL) were added, extracted and partitioned. The aqueous phase was extracted with dichloromethane (150 mL×2). The organic phase was combined and washed with saturated aqueous sodium bicarbonate solution (200 mL×3), dried over anhydrous sodium sulfate and concentrated in vacuo. The residue was separated by silica gel column chromatography (eluent: petroleum ether/ethyl acetate=30:1 to 10:1) to obtain the compound 6-bromo-2-chloro-8-cyclopentyl-5-methyl-8H-pyrido[2,3-d] pyrimidin-7-one (21.5 g, yield: 83.1%). LCMS (ESI): m/z 344 [M+1]$^+$.

Step 1e: Preparation of tert-butyl-4-(6-aminopyridin-3-yl)piperidine-1-carboxylate (Compound 107)

5-Bromo-2-nitropyridine (107A) (2.6 g, 12.8 mmol, 1.0 eq), tert-butyl-4-(4,4,5,5-tetramethyl-1,3,2-dioxaborolan-2-yl)-3,6-dihydropyridine-1(2H)-carboxylate (107B) (4.8 g, 15.5 mmol, 1.2 eq), bis(triphenylphosphine)palladium(II) chloride (0.9 g, 1.28 mol, 0.1 eq) and cesium carbonate (8.4 g, 25.8 mmol, 2.0 eq) were dissolved in 15 mL of water and 150 mL of N,N-dimethylformamide. Under nitrogen protection, the reaction system was placed in a pre-heated 90° C. oil bath and reacted for 1 hour. After the reaction was completed, the reaction system was cooled to room temperature and extracted with ethyl acetate. The organic phase was washed with saturated brine several times, dried over anhydrous sodium sulfate, concentrated in vacuo and finally purified by silica gel column chromatography (eluent: petroleum ether/ethyl acetate=10:1 to 3:1) to obtain a yellow solid, which was tert-butyl 6-nitro-3',6'-dihydro-[3,4'-bipyridine]-1'(2'H)-carboxylate (107C) (3.53 g, yield: 90%). LCMS (ESI): m/z 306 [M+1]+.

Compound 107C from above (3.53 g, 11.6 mmol, 1.0 eq) was dissolved in 100 mL of methanol and palladium-on-carbon (0.353 g) was then added. Under hydrogen condition, the reaction was stirred at room temperature overnight. After the reaction was completed, the reaction was filtered to remove the palladium-on-carbon in the reaction solution and washed with methanol several times. The filtrate was concentrated in vacuo and finally purified by silica gel column chromatography (eluent: dichloromethane/methanol=100:1 to 30:1) to obtain a yellow solid, which was tert-butyl-4-(6-aminopyridin-3-yl) piperidine-1-carboxylate (2.5 g, yield: 78%). LCMS (ESI): m/z 278 [M+1]$^+$.

Step 1f: Preparation of tert-butyl 4-(6-((6-bromo-8-cyclopentyl-5-methyl-7-oxo-7,8-dihydropyrido[2,3-d]pyrimidin-2-yl)amino)pyridin-3-yl)piperidine-1-carboxylate (Compound 108)

Compound tert-butyl-4-(6-aminopyridin-3-yl)piperidine-1-carboxylate (107) (2.5 g, 9.0 mmol, 2.25 eq) was dissolved in 80 mL of anhydrous tetrahydrofuran and placed in an ice-water bath. Under nitrogen protection, sodium hydride (0.452 g, 10.8 mol, 2.7 eq) was added and the reaction was stirred for 15 minutes in the ice bath. To the reaction system was then added a solution of 6-bromo-2-chloro-8-cyclopentyl-5-methyl-8H-pyrido[2,3-d]pyrimidin-7-one (106) (1.4 g, 4 mmol, 2.7 eq) in 30 mL of tetrahydrofuran dropwise and stirred at room temperature overnight. The reaction was quenched with water, concentrated in vacuo and finally purified by silica gel column chromatography (eluent: dichloromethane/methanol=100:1 to 30:1) to obtain a yellow solid, which was tert-butyl4-(6-((6-bromo-8-cyclopentyl-5-methyl-7-oxo-7,8-dihydropyrido[2,3-d]pyrimidin-2-yl)amino)pyridin-3-yl)piperidine-1-carboxylate (2.145 g). LCMS (ESI): m/z 583 [M+1]$^+$.

Step 1g: Preparation of tert-butyl 4-(6-((8-cyclopentyl-6-(1-ethoxyvinyl)-5-methyl-7-oxo-7,8-dihydropyrido[2,3-d]pyrimidin-2-yl)amino)pyridin-3-yl) piperidin-1-carboxylate (Compound 109)

Compound tert-butyl 4-(6-((6-bromo-8-cyclopentyl-5-methyl-7-oxo-7,8-dihydropyrido[2,3-d]pyrimidin-2-yl) amino)pyridin-3-yl)piperidine-1-carboxylate (108) (300 mg, 0.515 mmol, 1.0 eq), tetrakis(triphenylphosphine)palladium(0) (54 mg, 0.051 mmol, 0.1 eq) and 1-ethoxyvinyl-tri-n-butyltin (371 mg, 1.03 mmol, 2.0 eq) were dissolved in 40 mL of toluene. Under nitrogen protection, the reaction was heated to 130° C. and refluxed overnight. After the reaction was completed, the reaction system was cooled to room temperature, concentrated in vacuo and finally purified by silica gel column chromatography (eluent: dichloromethane/methanol=100:1 to 30:1) to obtain a yellow solid, which was tert-butyl 4-(6-((8-cyclopentyl-6-(1-ethoxyvinyl)-5-methyl-7-oxo-7,8-dihydropyrido[2,3-d]pyrimidin-2-yl)amino)pyridin-3-yl)piperidin-1-carboxylate (150 mg, yield: 51%). LCMS (ESI): m/z 575 [M+1]$^+$.

Step 1h: Preparation of 6-acetyl-8-cyclopentyl-5-methyl-2-((5-(piperidin-4-yl)pyridin-2-yl)amino) pyrido[2,3-d]pyrimidin-7(8H)-one (Compound 110)

tert-Butyl 4-(6-((8-cyclopentyl-6-(1-ethoxyvinyl)-5-methyl-7-oxo-7,8-dihydropyrido[2,3-d]pyrimidin-2-yl)amino)pyridin-3-yl)piperidin-1-carboxylate (109) (150 mg, 0.261 mmol) was dissolved in 100 mL of dichloromethane and 4 mL of 6 mol/L hydrochloric acid was added and stirred at room temperature for 2 hours. After the reaction was completed, the pH was adjusted to 8-9 by an addition of saturated aqueous sodium bicarbonate solution and then filtered to remove the inorganic salts generated. The filtrate was concentrated in vacuo and finally purified by silica gel column chromatography (eluent: dichloromethane/methanol=100:1 to 15:1) to obtain a white solid, which was 6-acetyl-8-cyclopentyl-5-methyl-2-((5-(piperidin-4-yl)pyridin-2-yl)amino)pyrido[2,3-d]pyrimidin-7(8H)-one (80 mg, yield: 62%). LCMS (ESI): m/z 447 [M+1]$^+$. $^1$H NMR (500 MHz, DMSO-d$_6$): δ 10.21 (s, 1H), 8.99 (s, 1H), 8.22 (s, 1H), 7.98 (d, J=8.5 Hz, 1H), 7.69 (d, J=8.6 Hz, 1H), 5.84 (m, 1H), 3.03 (d, J=11.9 Hz, 2H), 2.60 (dd, J=23.9, 11.9 Hz, 3H), 2.43 (s, 3H), 2.32 (s, 3H), 2.26 (s, 3H), 1.90 (s, 2H), 1.79 (s, 2H), 1.70 (d, J=12.0 Hz, 2H), 1.55 (ddd, J=21.3, 11.3, 7.0 Hz, 4H).

Step 1i: Preparation of 2-(methylsulfonyl)ethyl methanesulfonate (Compound 111-1)

Under nitrogen protection, 2-(methanesulfonyl)ethanol (143 mg, 1.15 mmol, 1.0 eq) was dissolved in 20 mL of dichloromethane and methanesulfonyl chloride (144 mg, 1.26 mmol, 1.1 eq) was added dropwise at room temperature followed by an addition of triethylamine (349 mg, 3.45 mmol, 3.0 eq). The mixture was stirred at 40° C. for 20 hours and then cooled to room temperature. The reaction solution was washed with aqueous sodium bicarbonate solution and dried to give a dichloromethane solution of 2-(methylsulfonyl)ethyl methanesulfonate (0.056M, 20 mL), which was used for the next step directly.

Step 1j: Preparation of 6-acetyl-8-cyclopentyl-5-methyl-2-((5-(1-(2-(methylsulfonyl)ethyl)piperidin-4-yl)pyridin-2-yl)amino)pyrido[2,3-d]pyrimidin-7(8H)-one (Compound 1)

Compound 6-acetyl-8-cyclopentyl-5-methyl-2-((5-(piperidin-4-yl) pyridin-2-yl)amino)pyrido[2,3-d]pyrimidin-7(8H)-one (110) (100 mg, 0.22 mmol, 1.0 eq) was dissolved in acetonitrile (30 mL) and potassium carbonate (30 mg, 0.22 mmol, 1.0 eq) was added. Under nitrogen protection, the reaction was heated to 80° C. and 2-(methylsulfonyl)ethyl methanesulfonate solution (111-1) (50 mL, 0.28 mmol, 1.2 eq) was added dropwise slowly and stirred at 80° C. for 4 hours and then cooled to room temperature. The reaction solution was extracted with dichloromethane and water and partitioned. The organic phase was washed with water, dried over anhydrous sodium sulfate and concentrated to give the crude product as a yellow solid which was separated and purified by silica gel column chromatography (eluent: dichloromethane/methanol=100:1 to 10:1) to obtain 6-acetyl-8-cyclopentyl-5-methyl-2-((5-(1-(2-(methylsulfonyl)ethyl)piperidin-4-yl) pyridin-2-yl)amino)pyrido[2,3-d]pyrimidin-7(8H)-one as a white solid (80 mg, yield: 65.8%). LCMS (ESI): m/z 553 [M+1]$^+$. m.p.: 256.3-260.2° C.; $^1$H NMR (500 MHz, DMSO-d6) δ 10.21 (s, 1H), 8.99 (s, 1H), 8.24 (s, 1H), 7.98 (d, J=8.5 Hz, 1H), 7.73 (d, J=8.5 Hz, 1H), 5.84 (p, J=9.0 Hz, 1H), 3.31 (d, J=6.5 Hz, 2H), 3.03 (m, 5H), 2.75 (t, J=6.5 Hz, 2H), 2.55 (d, J=14.9 Hz, 1H), 2.43 (s, 3H), 2.32 (s, 3H), 2.26 (s, 2H), 2.09 (t, J=11.3 Hz, 2H), 1.90 (s, 2H), 1.79 (d, J=10.2 Hz, 4H), 1.65 (m, 4H).

Example 2

Preparation of 6-acetyl-8-cyclopentyl-5-methyl-2-((5-(1-(3-(methylsulfonyl) propyl)piperidin-4-yl) pyridin-2-yl)amino)pyrido[2,3-d]pyrimidin-7(8H)-one (Compound 2)

Step 2a: Preparation of 1-bromo-3-(methylsulfonyl)propane (Compound 112-2

Under nitrogen protection, 3-(methylsulfonyl)propan-1-ol (50 mg, 0.36 mmol, 1.0 eq) was dissolved in 10 mL of dichloromethane, and in an ice bath condition, phosphorus tribromide (0.04 mL, 0.43 mmol, 1.2 eq) was added dropwise. The reaction solution was then warmed to room temperature and stirred to react for 15 hours. The reaction solution was added slowly into ice water and then the mixture was extracted with dichloromethane and partitioned. The organic phase was washed with water, dried and concentrated to give 1-bromo-3-(methylsulfonyl)propane as a colorless oily liquid (49 mg, yield: 68%).

Step 2b: Preparation of 6-acetyl-8-cyclopentyl-5-methyl-2-((5-(1-(3-(methylsulfonyl)propyl)piperidin-4-yl)pyridin-2-yl)amino)pyrido[2,3-d]pyrimidin-7(8H)-one (Compound 2)

Compound 6-acetyl-8-cyclopentyl-5-methyl-2-((5-(piperidin-4-yl) pyridin-2-yl)amino)pyrido[2,3-d]pyrimidin-7(8H)-one (110) (30 mg, 0.067 mmol, 1.0 eq) was dissolved in acetonitrile (20 mL) and potassium carbonate (18 mg, 0.134 mmol, 2.0 eq) was added. Then 1-bromo-3-(methylsulfonyl)propane (112-2) solution (20 mg, 0.1 mmol, 1.5 eq) was added dropwise slowly. Under nitrogen protection, the reaction was heated to 80° C. and stirred for 4 hours and then cooled to room temperature. The reaction was extracted with dichloromethane and water and partitioned. The organic phase was washed with water, dried over anhydrous sodium sulfate and concentrated to give a crude product which was separated and purified by silica gel column chromatography (eluent: dichloromethane/methanol=100:1 to 10:1) to obtain compound 6-acetyl-8-cyclopentyl-5-methyl-2-((5-(1-(3-(methylsulfonyl) propyl)piperidin-4-yl)pyridin-2-yl)amino) pyrido[2,3-d]pyrimidin-7(8H)-one as a white solid (10 mg, yield: 26.4%). LCMS(ESI): m/z 567[M+1]$^+$. $^1$H NMR (500 MHz, DMSO-d6) δ 10.21 (s, 1H), 8.99 (s, 1H), 8.24 (d, J=2.3 Hz, 1H), 7.99 (d, J=8.6 Hz, 1H), 7.73 (dd, J=8.6, 2.4 Hz, 1H), 5.84 (m, 1H), 3.13 (m, 2H), 2.97 (d, J=13.3 Hz, 5H), 2.55 (dd, J=9.6, 6.0 Hz, 1H), 2.43 (m, 5H), 2.32 (s, 3H), 2.27 (m, 2H), 2.03 (t, J=10.8 Hz, 2H), 1.87 (m, 4H), 1.78 (d, J=10.4 Hz, 4H), 1.70 (td, J=12.3, 3.3 Hz, 2H), 1.60 (m, 2H).

Example 3

Preparation of 6-acetyl-2-((5-(1-(2-((4-chlorophenyl)sulfonyl)ethyl) piperidin-4-yl)pyridin-2-yl)amino)-8-cyclopentyl-5-methylpyrido[2,3-d]pyrimidin-7 (8H)-one (Compound 4)

Step 3a: Preparation of 1-((2-bromoethyl)sulfonyl)-4-chlorobenzene (Compound 112-4)

1,2-Dibromoethane (4.7 g, 25 mmol, 5.0 eq) was dissolved in 100 mL of acetonitrile and potassium carbonate (828 mg, 6.0 mmol, 1.2 eq) was added at room temperature followed by an addition of a solution of 4-chlorothiophenol (720 mg, 5.0 mmol, 1.0 eq) in acetonitrile (10 mL) slowly. The reaction was stirred at room temperature for 2 hours, and then extracted with ethyl acetate and water and partitioned. The organic phase was washed with water, dried over anhydrous sodium sulfate and concentrated to obtain the crude product which was separated and purified by silica gel column chromatography (eluent: petroleum ether/ethyl acetate=100:1) to obtain (2-bromoethyl)(4-chlorophenyl) sulfane (1.0 g, yield: 80%). The obtained (2-bromoethyl)(4-chlorophenyl)sulfane was dissolved in 100 mL of dichloromethane and 3-chloroperbenzoic acid (2.06 mg, 12 mmol, 3.0 eq) was added in batches under an ice bath condition, and stirred at room temperature for 2 hours. The reaction solution was extracted with ethyl acetate and water and partitioned. The organic phase was washed with water, dried over anhydrous sodium sulfate and concentrated to give the crude product which was separated and purified by silica gel column chromatography (eluent: petroleum ether/ethyl acetate=100:1 to 30:1) to obtain compound 1-((2-bromoethyl)sulfonyl)-4-chlorobenzene (500 mg, yield: 44%).

Step 3b: Preparation of 6-acetyl-2-((5-(1-(2-((4-chlorophenyl) sulfonyl)ethyl)piperidin-4-yl)pyridin-2-yl)amino)-8-cyclopentyl-5-methylpyrido[2,3-d]pyrimidin-7(8H)-one (Compound 4)

Compound 6-acetyl-8-cyclopentyl-5-methyl-2-((5-(piperidin-4-yl) pyridin-2-yl)amino)pyrido[2,3-d]pyrimidin-7 (8H)-one (110) (100 mg, 0.22 mmol, 1.0 eq) was dissolved in N,N-dimethylformamide (30 mL) and heated to 80° C. under nitrogen protection. After the solid was dissolved completely, the reaction solution was cooled to room temperature and potassium carbonate (30 mg, 0.22 mmol, 1.0 eq) was then added and followed by an addition of a solution of 1-((2-bromoethyl)sulfonyl)-4-chlorobenzene (112-4) (80 mg, 0.28 mmol, 1.2 eq) in 2 mL of acetonitrile slowly. The reaction was stirred at 40° C. for 4 hours and then cooled to room temperature. The reaction solution was extracted with dichloromethane and water and partitioned. The organic phase was washed with water, dried over anhydrous sodium sulfate, and concentrated to obtain a crude product as a yellow solid which was separated and purified by silica gel column chromatography (eluent: dichloromethane/methanol=100:1 to 10:1) to obtain 6-acetyl-2-((5-(1-(2-((4-chlorophenyl)sulfonyl)ethyl)piperidin-4-yl)pyridin-2-yl)amino)-8-cyclopentyl-5-methylpyrido[2,3-d]pyrimidin-7 (8H)-one as a white solid (20 mg, yield: 14%). LCMS(ESI): m/z 649[M+1]$^+$. $^1$H NMR (500 MHz, DMSO-d6) δ 10.22 (s, 1H), 8.99 (s, 1H), 8.14 (d, J=2.2 Hz, 1H), 7.96 (m, 3H), 7.75 (d, J=8.6 Hz, 2H), 7.56 (dd, J=8.6, 2.3 Hz, 1H), 5.85 (m, 1H), 3.58 (t, J=6.3 Hz, 2H), 2.75 (d, J=11.0 Hz, 2H), 2.64 (t, J=6.3 Hz, 2H), 2.43 (s, 3H), 2.38 (s, 1H), 2.32 (s, 3H), 2.26 (dd, J=11.4, 7.9 Hz, 2H), 1.90 (dd, J=13.4, 8.0 Hz, 4H), 1.80 (m, 2H), 1.59 (m, 4H), 1.15 (dd, J=12.2, 3.0 Hz, 2H).

Example 4

Preparation of 6-acetyl-8-cyclopentyl-5-methyl-2-((5-(1-(2-(methylsulfonyl) ethyl)piperidin-3-yl)pyridin-2-yl)amino)pyrido[2,3-d]pyrimidin-7(8H)-one (Compound 5)

Step 4a: Preparation of 2-chloro-8-cyclopentyl-6-iodo-5-methylpyrido[2,3-d]pyrimidin-7(8H)-one (Compound 201)

2-Chloro-8-cyclopentyl-5-methyl-8H-pyrido[2,3-d]pyrimidin-7-one (105) (20 g, 76 mmol, 1.0 eq) was dissolved in 250 mL of trifluoroacetic acid and 10 mL of trifluoroacetic anhydride. Under nitrogen protection, N-iodosuccinimide (68.5 g, 304 mmol, 4.0 eq) was added and the mixture was heated to 80° C. After 1 hour, the reaction solution was concentrated in vacuo and sodium bisulfite solution was added to remove the remaining N-iodosuccinimide, extracted with dichloromethane and washed with saturated brine twice. The organic phase was dried over anhydrous sodium sulfate and concentrated in vacuo to obtain compound 2-chloro-8-cyclopentyl-6-iodo-5-methylpyrido[2,3-d]pyrimidin-7(8H)-one as a white solid (29 g, yield: 98.5%). LCMS(ESI): m/z 390[M+1]$^+$.

Step 4b: Preparation of 2-chloro-8-cyclopentyl-6-(1-ethoxyvinyl)-5-methylpyrido[2,3-d]pyrimidin-7 (8H)-one (Compound 202)

Under nitrogen protection, 2-chloro-8-cyclopentyl-6-iodo-5-methylpyrido[2,3-d]pyrimidin-7(8H)-one (201) (15 g, 38.56 mmol, 1.0 eq) and 1-ethoxyvinyltri-n-butyltin (13.8 g, 42.4 mmol, 1.1 eq) were dissolved in 150 mL of toluene and heated to 120° C. Bis(triphenylphosphine)palladium(II) chloride (2.43 g, 3.8 mmol, 0.1 eq) was added and reacted at 125° C. for 3 hours. The reaction solution was concentrated in vacuo to give a crude product which was purified by silica gel column chromatography (eluent: ethyl acetate/petroleum ether=1/10 to 1/5) to obtain 2-chloro-8-cyclopentyl-6-(1-ethoxyvinyl)-5-methylpyrido[2,3-d]pyrimidin-7 (8H)-one as a brown solid (282 mg, yield: 18.5%). LCMS (ESI): m/z 334 [M+1]$^+$.

Step 4c: Preparation of tert-butyl3-(6-aminopyridin-3-yl)piperidine-1-carboxylate (Compound 203)

5-Bromo-2-nitropyridine (107A) (1.0 g, 4.98 mmol, 1.0 eq), bis(triphenylphosphine)palladium(II) chloride (174 mg, 0.25 mmol, 0.05 eq) and anhydrous cesium carbonate (2.43 g, 7.47 mmol, 1.5 eq) were mixed in 5 mL of water and 50 mL of N,N-dimethylformamide. Under nitrogen protection, compound tert-butyl 5-(4,4,5,5-tetramethyl-1,3,2-dioxaborolan-2-yl)-3,4-dihydropyridine-1(2H)-carboxylate (203A) (2.13 g, 6.89 mmol, 1.4 eq) was added and heated to 85° C. After 1 hour, the reaction was cooled to room temperature, extracted with ethyl acetate and washed with saturated brine twice. The organic phase was dried over anhydrous sodium sulfate and concentrated in vacuo to obtain the crude product which was purified by silica gel column chromatography (eluent: ethyl acetate/petroleum ether=10/100 to 50/100) to obtain a yellow solid, which was compound tert-butyl 6'-nitro-5,6-dihydro-[3,3'-bipyridine]-1 (4H)-carboxylate (203B) (282 mg, yield: 18.5%). LCMS (ESI): m/z 306 [M+1]⁺.

Under hydrogen protection, the compound 203B prepared above (100 mg, 0.33 mmol, 1.0 eq) and palladium-on-carbon (10 mg, 10%) were added into a reaction flask containing methanol (10 mL) and stirred at 30° C. overnight. After filtration, the filtrate was concentrated in vacuo to give compound tert-butyl 3-(6-aminopyridin-3-yl)piperidine-1-carboxylate (89 mg, crude, used for the next step directly). LCMS (ESI): m/z 278 [M+1]⁺.

Step 4d: Preparation of tert-butyl 3-(6-((8-cyclopentyl-6-(1-ethoxyvinyl)-5-methyl-7-oxo-7,8-dihydropyrido[2,3-d]pyrimidin-2-yl)amino) pyridin-3-yl) piperidine-1-carboxylate (Compound 204)

Under nitrogen protection, compound tert-butyl 3-(6-aminopyridin-3-yl)piperidine-1-carboxylate (203) (89 mg, 0.32 mmol, 1.0 eq), compound 2-chloro-8-cyclopentyl-6-(1-ethoxyvinyl)-5-methylpyrido[2,3-d]pyrimidin-7(8H)-one (202) (106 mg, 0.32 mmol, 1.0 eq), 4,5-bis(diphenylphosphino)-9,9-dimethylxanthene (17 mg, 0.029 mmol, 0.09 eq), cesium carbonate (156 mg, 0.48 mmol, 2.0 eq) and tris (dibenzylideneacetone)dipalladium (15 mg, 0.016 mmol, 0.05 eq) were added into a reaction flask containing toluene and heated to 90° C. to stir for 5 hours. The reaction solution was concentrated in vacuo to give a crude product which was separated and purified by silica gel column chromatography (eluent: methanol/dichloromethane=0/100 to 5/100) to obtain tert-butyl 3-(6-((8-cyclopentyl-6-(1-ethoxyvinyl)-5-methyl-7-oxo-7,8-dihydropyrido[2,3-d]pyrimidin-2-yl) amino)pyridin-3-yl)piperidine-1-carboxylate as a yellow colloid (96 mg, yield: 52.2%). LCMS (ESI): m/z 575 [M+1]⁺.

Step 4e: Preparation of 6-acetyl-8-cyclopentyl-5-methyl-2-((5-(piperidin-3-yl) pyridin-2-yl)amino) pyrido[2,3-d]pyrimidin-7(8H)-one (Compound 205)

Compound tert-butyl 3-(6-((8-cyclopentyl-6-(1-ethoxyvinyl)-5-methyl-7-oxo-7,8-dihydropyrido[2,3-d]pyrimidin-2-yl)amino)pyridin-3-yl)piperidine-1-carboxylate (204) (96 mg, 0.167 mmol, 1.0 eq) was dissolved in dichloromethane (50 mL) and hydrochloric acid-methanol solution (5 mL) was added dropwise slowly. After stirring for 3 hours, the solvent was removed in vacuo to give compound 6-acetyl-8-cyclopentyl-5-methyl-2-((5-(piperidin-3-yl)pyridin-2-yl) amino)pyrido[2,3-d]pyrimidin-7(8H)-one (83 mg, crude), which was used for the next step directly. LCMS(ESI): m/z 447[M+1]⁺.

Step 4f: Preparation of 6-acetyl-8-cyclopentyl-5-methyl-2-((5-(1-(2-(methylsulfonyl)ethyl)piperidin-3-yl)pyridin-2-yl)amino)pyrido[2,3-d]pyrimidin-7 (8H)-one (Compound 5)

Compound 6-acetyl-8-cyclopentyl-5-methyl-2-((5-(piperidin-3-yl) pyridin-2-yl)amino)pyrido[2,3-d]pyrimidin-7 (8H)-one (205) (60 mg, 0.134 mmol, 1.0 eq) was dissolved in acetonitrile (30 mL) and potassium carbonate (18 mg, 0.134 mmol, 1.0 eq) was added. Under nitrogen protection, the reaction was heated to 70° C. and a solution of 2-(methylsulfonyl)ethyl methanesulfonate (111-1) in dichloromethane (3 mL, 0.161 mmol, 1.2 eq) was added dropwise slowly. It was then stirred at 70° C. for 3 hours and cooled to room temperature. The reaction was extracted with dichloromethane and water and partitioned. The organic phase was washed with water, dried over anhydrous sodium sulfate, and concentrated to give crude product as a yellow solid which was separated and purified by silica gel column chromatography (eluent: dichloromethane/methanol=100:1 to 10:1) to obtain compound 6-acetyl-8-cyclopentyl-5-methyl-2-((5-(1-(2-(methylsulfonyl)ethyl) piperidin-3-yl) pyridin-2-yl)amino)pyrido[2,3-d]pyrimidin-7(8H)-one as a yellow solid (58 mg, yield: 78.4%). LCMS (ESI): m/z 553 [M+1]⁺. m.p.: 109-113° C.; ¹H NMR (500 MHz, DMSO-d6) δ 10.24 (s, 1H), 9.00 (s, 1H), 8.27 (d, J=2.2 Hz, 1H), 8.01 (d, J=8.6 Hz, 1H), 7.75 (dd, J=8.6, 2.3 Hz, 1H), 5.85 (m, 1H), 3.31 (dd, J=6.6, 2.8 Hz, 2H), 3.03 (s, 3H), 2.93 (dd, J=23.9, 11.2 Hz, 2H), 2.77 (m, 3H), 2.43 (s, 3H), 2.32 (s, 3H), 2.27 (m, 2H), 2.07 (dt, J=11.3, 10.0 Hz, 2H), 1.92 (dd, J=7.6, 5.5 Hz, 2H), 1.78 (m, 4H), 1.60 (dd, J=13.8, 8.9 Hz, 3H), 1.47 (dd, J=12.2, 3.5 Hz, 1H).

Example 5

Preparation of 3-acetyl-1-cyclopentyl-4-methyl-7-((5-(1-(2-(methylsulfonyl) ethyl)piperidin-4-yl)pyridin-2-yl)amino)-1,6-naphthyridin-2(1H)-one (Compound 13)

Step 5a: Preparation of 2-chloro-5-iodopyridin-4-amine (Compound 302)

Under nitrogen protection, 2-chloropyridin-4-amine (301) (15 g, 0.116 mol, 1 eq) was dissolved in acetonitrile (200 mL) and heated to 70° C. in an oil bath, and then N-iodosuccinimide (NIS) (33 g, 0.139 mol, 1.2 eq) was added slowly. The reaction was stirred for 16 hours and cooled to room temperature. Saturated sodium thiosulfate solution was added until the reaction system turned to milk white. The pH of the reaction system was adjusted to 9-10 by an addition of saturated aqueous sodium carbonate solution and extracted with ethyl acetate (500 mL). The organic phase was separated which was washed with saturated brine (100 mL) twice, dried over anhydrous sodium sulfate, concentrated in vacuo and separated and purified by silica gel column chromatography (eluent: petroleum ether/ethyl acetate=20/1) to obtain 2-chloro-5-iodopyridin-4-amine (23 g, yield: 78.1%). LCMS (ESI): m/z 255 [M+1]⁺.

Step 5b: Preparation of 2-chloro-N-cyclopentyl-5-iodopyridin-4-amine (Compound 303)

Under nitrogen protection, 2-chloro-5-iodopyridin-4-amine (302) (23 g, 90.6 mmol, 1 eq), cesium carbonate (177 g, 0.544 mol, 6 eq) and bromocyclopentane (81 g, 0.544 mol, 6 eq) were added into a reaction flask containing thionyl chloride (500 mL) as the solvent and heated to 90° C. to stir for 36 hours. The reaction was filtered and the filtrate was extracted with ethyl acetate. The organic phase was washed with water (500 mL) three times and saturated brine (400 mL) three times, dried over anhydrous sodium sulfate, concentrated in vacuo and separated and purified by silica gel column chromatography (eluent: petroleum ether/ ethyl acetate=10/1) to obtain 2-chloro-N-cyclopentyl-5-iodopyridin-4-amine (6 g, yield: 20.5%). LCMS (ESI): m/z 323 [M+1]⁺.

Step 5c: Preparation of ethyl (E)-3-(6-chloro-4-(cyclopentylamino)pyridin-3-yl)but-2-enoate (Compound 304)

Under nitrogen protection, 2-chloro-N-cyclopentyl-5-iodopyridin-4-amine (303) (6 g, 18.6 mmol, 1 eq), sodium carbonate (4.93 g, 46.5 mmol, 2.5 eq), (Z)-ethyl-3-(4,4,5,5-tetramethyl-1,3,2-dioxaborolan-2-yl)but-2-enoate (103) (5.8 g, 24.2 mmol, 1.3 eq) and bis(triphenylphosphine)palladium (II) chloride (0.9 g, 1.28 mol, 0.1 eq) were added into a reaction flask containing DMF and water (10:1) as the solvent. The reaction was heated to 90° C. and reacted for 3.5 hours. Ethyl acetate (400 mL) was added and washed with water (200 mL) three times and brine (100 mL) one time, and concentrated to give the crude product which was separated and purified by silica gel column chromatography (eluent: petroleum ether/ethyl acetate=4/1) to obtain ethyl (E)-3-(6-chloro-4-(cyclopentylamino)pyridin-3-yl)but-2-enoate (304) (5.2 g, yield: 90.9%). LCMS (ESI): m/z 309 [M+1]$^+$.

Step 5d: Preparation of 7-chloro-1-cyclopentyl-4-methyl-1,6-naphthyridin-2(1H)-one (Compound 305)

Ethyl (E)-3-(6-chloro-4-(cyclopentylamino) pyridin-3-yl) but-2-enoate (304) (5.2 g, 16.9 mmol, 1 eq) was dissolved in toluene (20 mL) and DBU (1,8-diazabicyclo[5.4.0]undec-7-ene) (2.57 g, 1.69 mmol, 0.1 eq) was added and heated to reflux and stir for 16 hours. The reaction was cooled to room temperature, concentrated and separated and purified by silica gel column chromatography (eluent: petroleum ether/ethyl acetate=15/1) to obtain 7-chloro-1-cyclopentyl-4-methyl-1,6-naphthyridin-2(1H)-one (3.7 g, yield: 83.4%). LCMS (ESI): m/z 263 [M+1]$^+$.

Step 5e: Preparation of 3-bromo-7-chloro-1-cyclopentyl-4-methyl-1,6-naphthyridin-2(1H)-one (Compound 306)

Compound 7-chloro-1-cyclopentyl-4-methyl-1,6-naphthyridin-2(1H)-one (305) (3.7 g, 14.1 mmol, 1 eq) was dissolved in glacial acetic acid (10 mL) and sodium acetate (4.62 g, 56.4 mmol, 4 eq) was added and heated to 50° C. Bromine (4.9 g, 15.5 mmol, 1.1 eq) was dissolved in acetic acid and was added dropwise slowly into the reaction flask. The reaction was stirred for 3.5 hours and cooled to room temperature. Saturated sodium thiosulfate solution was added slowly until the reaction turned to clear and then the pH of the reaction system was adjusted to 9-10 by an addition of saturated aqueous sodium carbonate solution. The mixture was extracted with dichloromethane (200 mL) and concentrated to give the crude product which was separated and purified by silica gel column chromatography (eluent: petroleum ether/ethyl acetate=10/1) to obtain 3-bromo-7-chloro-1-cyclopentyl-4-methyl-1,6-naphthyridin-2(1H)-one (3 g, yield: 62.6%). LCMS (ESI): m/z 341 [M+1]$^+$.

Step 5f: Preparation of 7-chloro-1-cyclopentyl-3-(1-ethoxyvinyl)-4-methyl-1,6-naphthyridin-2(1H)-one (Compound 307)

Under nitrogen protection, 3-bromo-7-chloro-1-cyclopentyl-4-methyl-1,6-naphthyridin-2(1H)-one (306) (1.5 g, 4.41 mmol, 1 eq), tetrakis(triphenylphosphine)palladium(0) (509 mg, 0.44 mmol, 0.1 eq) and 1-ethoxyvinyltri-n-butyltin (2.07 g, 5.73 mmol, 1.3 eq) were dissolved in toluene (20 mL) in a reaction flask and heated to reflux to react for 16 hours. The reaction was concentrated in vacuo to give the crude product which was separated and purified by silica gel column chromatography (eluent: petroleum ether/ethyl acetate=10/1) to obtain 7-chloro-1-cyclopentyl-3-(1-ethoxyvinyl)-4-methyl-1,6-naphthyridin-2(1H)-one (1.0 g, yield: 68.3%). LCMS (ESI): m/z 333 [M+1]$^+$.

Step 5g: Preparation of tert-butyl 4-(6-((1-cyclopentyl-3-(1-ethoxyvinyl)-4-methyl-2-oxo-1,2-dihydro-1,6-naphthyridin-7-yl)amino)pyridin-3-yl)piperidine-1-carboxylate (Compound 308)

7-Chloro-1-cyclopentyl-3-(1-ethoxyvinyl)-4-methyl-1,6-naphthyridin-2(1H)-one (307) (150 mg, 0.45 mmol, 1.0 eq), tert-butyl-4-(6-aminopyridin-3-yl) piperidine-1-carboxylate (107) (165 mg, 0.585 mmol, 1.3 eq), cesium carbonate (300 mg, 0.9 mmol, 2.0 eq) and 4,5-bis(diphenylphosphino)-9,9-dimethylxanthene (21 mg, 0.036 mmol, 0.08 eq) were dispersed in 30 mL of toluene. Under nitrogen protection, Pd$_2$(dba)$_3$ (tris(dibenzylideneacetone)dipalladium (16 mg, 0.018 mmol, 0.04 eq) was added. The reaction system was placed in a preheated 130° C. oil bath and reflux and stirred for 6 hours. After the reaction was completed, it was cooled to room temperature, concentrated in vacuo and finally purified by silica gel column chromatography (eluent: dichloromethane/methanol=100:1 to 15:1) to obtain a yellow solid, which was tert-butyl 4-(6-((1-cyclopentyl-3-(1-ethoxyvinyl)-4-methyl-2-oxo-1,2-dihydro-1,6-naphthyridin-7-yl)amino)pyridin-3-yl)piperidine-1-carboxylate (176 mg, yield: 68%). LCMS (ESI): m/z 574 [M+1]$^+$.

Step 5h: Preparation of 3-acetyl-1-cyclopentyl-4-methyl-7-((5-(piperidin-4-yl)pyridin-2-yl)amino)-1,6-naphthyridin-2(1H)-one (Compound 309)

Tert-butyl 4-(6-((1-cyclopentyl-3-(1-ethoxyvinyl)-4-methyl-2-oxo-1,2-dihydro-1,6-naphthyridin-7-yl)amino) pyridin-3-yl)piperidine-1-carboxylate (308) (176 mg, 0.307 mmol) was dissolved in 30 mL of dichloromethane and 6 mL of 6 mol/L hydrochloric acid was added and stirred at room temperature for 2 hours. To the reaction solution was added saturated sodium bicarbonate solution to adjust the pH to 8-9 and then filtered to remove the inorganic salts generated. The filtrate was concentrated in vacuo and finally purified by silica gel column chromatography (eluent: dichloromethane/methanol=100:1 to 10:1) to obtain a yellow solid, which was 3-acetyl-1-cyclopentyl-4-methyl-7-((5-(piperidin-4-yl)pyridin-2-yl) amino)-1,6-naphthyridin-2 (1H)-one (62 mg, yield: 45%). LCMS(ESI): m/z 446[M+1]$^+$. m.p.: 190.5-191.7° C.; $^1$H NMR (500 MHz, DMSO-d6) δ 10.08 (d, J=17.5 Hz, 1H), 8.77 (d, J=11.5 Hz, 1H), 8.30 (s, 1H), 8.14 (d, J=9.4 Hz, 1H), 7.61 (m, 1H), 7.41 (d, J=8.6 Hz, 1H), 5.70 (m, 1H), 3.36 (m, 3H), 2.98 (t, J=11.5 Hz, 1H), 2.86 (t, J=11.9 Hz, 1H), 2.43 (s, 3H), 2.36 (d, J=8.5 Hz, 3H), 2.26 (m, 4H), 1.85 (m, 8H).

Step 5i: Preparation of 3-acetyl-1-cyclopentyl-4-methyl-7-((5-(1-(2-(methylsulfonyl)ethyl)piperidin-4-yl)pyridin-2-yl)amino)-1,6-naphthyridin-2(1H)-one (Compound 13)

Compound 3-acetyl-1-cyclopentyl-4-methyl-7-((5-(piperidin-4-yl)pyridin-2-yl)amino)-1,6-naphthyridin-2(1H)-one (309) (140 mg, 0.31 mmol, 1.0 eq) was dissolved in acetonitrile (50 mL) and potassium carbonate (43 mg, 0.31 mmol, 1.0 eq) was added. After the reaction temperature was raised to 50° C., 2-(methylsulfonyl) ethyl methanesulfonate solution (111-1) (20.7 mL, 0.37 mmol, 1.2 eq) was added dropwise slowly. The reaction was then stirred at 80° C. for 2 hours, cooled to room temperature and extracted with dichloromethane and water and partitioned. The organic phase was washed with brine twice, dried over anhydrous sodium sulfate and concentrated to obtain the crude product as a yellow solid which was separated and purified by silica gel column chromatography (eluent: dichloromethane/methanol=100:1 to 10:1) to give 3-acetyl-1-cyclopentyl-4-methyl-7-((5-(1-(2-(methylsulfonyl)ethyl)piperidin-4-yl)pyridin-2-yl)amino)-1,6-naphthyridin-2(1H)-one as a yellow solid (117 mg, yield: 68.4%). LCMS (ESI): m/z 552 [M+1]$^+$. m.p.: 140.7-144.9° C.; $^1$H NMR (500 MHz, DMSO-d6) δ 10.03 (s, 1H), 8.77 (s, 1H), 8.28 (s, 1H), 8.13 (s, 1H), 7.63 (d, J=8.5 Hz, 1H), 7.37 (d, J=8.5 Hz, 1H), 5.68 (p, J=9.1 Hz, 1H), 3.31 (d, J=6.6 Hz, 2H), 3.05 (s, 3H), 3.01 (d, J=10.2 Hz, 2H), 2.74 (t, J=6.2 Hz, 2H), 2.51 (s, 1H), 2.43 (s, 3H), 2.34 (s, 3H), 2.24 (d, J=15.0 Hz, 2H), 2.18 (s, 2H), 2.08 (t, J=11.2 Hz, 2H), 1.89 (d, J=9.3 Hz, 2H), 1.76 (d, J=11.9 Hz, 4H), 1.63 (dd, J=22.7, 11.5 Hz, 2H).

Example 6 Biological Activity Test

I. Enzyme Activity Inhibition Experiment

1. Experimental Method (1) CDK2 Activity Inhibition Experiment

The activity of CDK2 protein kinase was measured using Caliper mobility shift assay (see J Biomol Screen 14: 31, 2009). The compounds obtained above were dissolved in DMSO and then diluted with kinase buffer solution (20 mM HEPES-pH 7.5, 0.01% Triton X-100, 10 mM MgCl$_2$, 2 mM DTT), 5 μl of the compounds at five times the final concentration dissolved in 10% DMSO were added to a 384 well plate, no compound control well was 5 μl of 10% DMSO, no enzyme activity control well was 5 μl of kinase buffer solution. 10 μl of the 2.5 times diluted CDK2 enzyme solution (Carna, Cat. No. 04-103) was added and then incubated at room temperature for 10 minutes, then 10 μl of the 2.5 times diluted substrate solution Peptide FAM-P18 (GL Biochem, Cat. No. 114202) was added. After being incubated at 28° C. for 60 minutes, 25 μl of stop solution was added to stop the reaction. Conversion rate data was read from Caliper EZ Reader II (Caliper Life Sciences). The conversion rate data was converted into inhibition rate data. Wherein max refers to the conversion rate of DMSO control well without compound and min refers to the conversion rate of no enzyme activity control well. The curve was plotted with compound concentration and inhibition rate as horizontal and vertical coordinates, and the IC$_{50}$ was calculated by fitting the curve using XLFit excel add-in version 4.3.1 software. Inhibition rate %=(max-conversion rate)/(max-min)×100.

(2) CDK4 Activity Inhibition Experiment

The activity of CDK2 protein kinase was measured using Caliper mobility shift assay (see J Biomol Screen 14:31, 2009). The compounds obtained above were dissolved in DMSO and then diluted with kinase buffer solution (20 mM HEPES-pH 7.5, 0.01% Triton X-100, 10 mM MgCl$_2$, 2 mM DTT), 5 μl of the compounds at five times the final concentration dissolved in 10% DMSO were added to a 384 well plate, no compound control well was 5 μl of 10% DMSO, no enzyme activity control well was 5 μl of kinase buffer solution. 10 μl of the 2.5 times diluted CDK4 enzyme solution (GST-CDK4(1-303end)/GST-CycD3 (1-292end; Carna, Cat. No. 04-105) was added and then incubated at room temperature for 10 minutes, then 10 μl of the 2.5 times diluted substrate solution Peptide FAM-P8 (GL Biochem, Cat. No. 112396) was added. After being incubated at 28° C. for 3 hours, 25 μl of stop solution was added to stop the reaction. Conversion rate data was read from Caliper EZ Reader II (Caliper Life Sciences). Conversion rate data was converted into inhibition rate data according to the method described above. Inhibition rate %=(max-conversion rate)/(max-min)×100.

(3) CDK6 Activity Inhibition Experiment

The activity of CDK6 protein kinase was measured using Caliper mobility shift assay (see J. Biomol Screen 14:31, 2009). The compounds obtained above were dissolved in DMSO and then diluted with kinase buffer solution (20 mM HEPES-pH 7.5, 0.01% Triton X-100, 10 mM MgCl$_2$, 2 mM DTT), 5 μl of the compounds at five times the final concentration dissolved in 10% DMSO were added to a 384 well plate, no compound control well was 5 μl of 10% DMSO, no enzyme activity control well was 5 μl of kinase buffer solution. 10 μl of the 2.5 times diluted CDK6 enzyme solution (GST-CDK6(1-326end); Carna, Cat. No 04-107) was added and then incubated at room temperature for 10 minutes, then 10 μl of the 2.5 times diluted substrate solution Peptide FAM-P8 (GL Biochem, Cat. No. 112396) was added. After being incubated at 28° C. for 40 minutes, 25 μl of stop solution was added to stop the reaction. Conversion rate data was read from Caliper EZ Reader II (Caliper Life Sciences). The conversion rate data was converted into inhibition rate data. Wherein max refers to the conversion rate of DMSO control (without compound) and min refers to the conversion rate of no enzyme activity control. Conversion rate data was converted into inhibition rate data according to the method described above. Inhibition rate %=(max−conversion rate)/(max−min)×100.

2. Experimental Results

The above experimental results are shown in the following table.

TABLE 1

Results of enzyme activity inhibition

| Compound | CDK6 | CDK4 | CDK2 | Compound | CDK6 | CDK4 | CDK2 |
|---|---|---|---|---|---|---|---|
| 1 | IV | V | I | 2 | IV | V | I |
| 4 | I | | | 5 | IV | IV | I |
| 13 | IV | V | I | | | | |
| PD-0332991 | V | V | I | | | | |
| LY2835219 | IV | V | IV | | | | |
| LEE011 | III | | | | | | |

Note:
I means IC$_{50}$ >500 nM,
II means 500 nM ≥ IC$_{50}$ > 100 nM,
III means 100 nM ≥ IC$_{50}$ > 50 nM,
IV means 50 nM ≥ IC$_{50}$ > 10 nM, and
V means IC$_{50}$ ≤10 nM.

From the above results, it can be seen that the compounds provided by the present disclosure have the IC$_{50}$ of I for CDK2 inhibition, i.e. at least >500 nM, with almost no inhibitory activity, the IC$_{50}$ of less than 50 nM for CDK6 inhibition (except for Compound 4), and the IC$_{50}$ of less than 10 nM for CDK4 inhibition. That is, the compounds can selectively inhibit CDK4 and CDK6 with almost no inhibitory activity on CDK2, and have higher inhibitory activities on CDK4 and CDK6 reaching 50 nM, or even below 10 nM, with characteristics of high selectivity and high activity.

II. Tumor Cell Proliferation Inhibition Experiment

1. Experimental Method

The content of adenosine triphosphate (ATP) was determined using the CellTiter-Glo Luminescent Cell Viability Assay Kit (Promega, Madison, Wis.) to evaluate cell viability. Tumor cell lines (SW620, ZR-75-1, MDA-MB-231) were purchased from the Cell Resource Center of IBS, Fudan University, Shanghai and the American Type Culture Collection (ATCC). The cell density was determined using Scepter automated cell counter (Millipore # PHCC00000) after the cells were digested with pancreatin in cell culture dishes and resuspended in DPBS medium. The cells were diluted to a solution of 44,000 cells per ml. The cell solution of which density was adjusted was added into the cell assay plate at 90 microliters per well. The well plate was incubated in an incubator with 5% CO$_2$ at 37° C. for 24 hours and then added with test compounds with different concentrations. The cells were incubated with the compounds in the presence of 10% fetal bovine serum for 72 hours. ATP content was assayed using the CellTiter-Glo® Luminescent Cell Viability Assay kit (see instructions of manufacturer) to assess cell growth inhibition. Briefly, 30 μl of CellTiter-Glo® reagent was added to each well, rocked for 10 minutes to induce cell lysis, and fluorescence signals were detected and recorded with Fluoroskan Ascent FL (Thermo). The maximum signal value was obtained from the cells treated with dimethyl sulfoxide for 72 hours. The minimum signal value was obtained from the separate culture medium (cell number was zero). Inhibition rate %=(maximum signal value−compound signal value)/(maximum signal value−minimum signal value)×100. Data was processed using GraphPad Prism V5.0 (GraphPad Software, San Diego, Calif.) software. IC$_{50}$ values were calculated by fitting S-shaped dose-response curves.

2. Experimental Results

The above experimental results are shown in the following table.

TABLE 2

Results of tumor cell proliferation inhibition

| Compound | SW620 | ZR-75-1 | MDA-MB-231 |
|---|---|---|---|
| 1 | IV | IV | IV |
| 2 | IV | V | IV |
| 5 | IV | IV | III |
| 13 | II | III | III |
| PD-0332991 | IV | IV | IV |
| LY2835219 | IV | V | IV |
| LEE011 | III | V | II |

Note:
I means IC$_{50}$ > 5 μM,
II means 5 μM ≥ IC$_{50}$ > 1 μM,
III means 1 μM ≥ IC$_{50}$ > 0.5 μM,
IV means 0.5 μM ≥ IC$_{50}$ > 0.1 μM and
V means IC$_{50}$ ≤ 0.1 μM.

From the above results, it can be seen that the compounds provided by the present disclosure have inhibitory activities on SW620, ZR-75-1, MDA-MB-231 tumor cell lines, and some compounds have higher activities.

III. Cell Cycle Inhibition Experiment

1. Experimental Method

The cell cycle and apoptosis assay kit (Beyotime, C1052) used in this experiment is an assay kit for analyzing the cell cycle and apoptosis using the classic method of Propidium staining (PI staining). Propidium (PI) is a double-stranded DNA fluorescent dye. The combination of propidium and double-stranded DNA can produce fluorescence, and fluorescence intensity is proportional to the amount of double-stranded DNA. After DNA in cells is stained with propidium, the DNA content of the cells can be measured by flow cytometry, and then the cell cycle and apoptosis can be analyzed according to the distribution of DNA content.

MDA-MB-231 cells were seeded into a 6-well plate at 3×10$^5$ per well and cultured for 24 hours. After the addition of the compounds to be tested or controls (PD-0332991 or LY2835219) for 24 h, the cells were centrifuged at 1000 rcf for 3 min and then collected and washed twice with PBS (phosphate buffer solution); the cells were fixed at 4° C. overnight with addition of precooled 70% ethanol, and then centrifuged at 1000 rcf for 10 min and washed twice with 1×PBS; and stained with PI staining solution for 30 min; and G1 cell cycle arrest was detected and analyzed by flow cytometry.

2. Experimental Results

In tumor cell cycle, the binding of CDK4 and CDK6 to cyclin D promotes G1 phase into S phase. CDK4/6 inhibitor selectively arrests the G1 phase of tumor cells into S phase. The detection results of the cell cycle of MDA-MB-231 breast cancer cells by flow cytometry indicate that the CDK4/6 inhibitor compounds provided by the present disclosure stop the growth of G1 phase cells and reduce S phase cells in a concentration-dependent manner, as shown in the following table.

TABLE 3

Results of the cell cycle experiment

| | IC$_{50}$ (nM) | |
|---|---|---|
| Compound | G1 arrest | S decrease |
| PD-0332991 | 42.4 ± 16.1 | 45.1 ± 10.9 |
| LY2835219 | 35.2 ± 8.9 | 42.9 ± 13.5 |
| Compound 1 | 41.7 | 46.1 |
| Compound 2 | 39.8 | 40.9 |

IV. Western Blot Experiment

1. Experimental Method

MDA-MB-231 cells were grown in monolayer culture. After incubation with the compounds to be tested or control compounds (PD-0332991 or LY2835219) for 16 hours, the cells were washed twice with precooled PBS and collected, and then homogenized 2-3 times with a biological sample homogenizer, and then centrifuged at 13,000 rpm for 10 min at 4° C., finally take the supernatant. The protein concentration was determined by the Branfor method. After being added with a loading buffer (Beyotime, # P0015L), the supernatant was boiled at 100° C. for 8 min, and the protein was separated by 8%-10% SDS-PAGE electrophoresis and then transferred to the PVDF membrane, and the membrane was blocked with 5% skimmed milk powder for 45 min, and then the cells were incubated overnight at 4° C. with primary antibody β-actin (CST, #4970), Rb (D20) Rabbit mAb (CST, #9313), Phospho-Rb(Ser780)(D59B7) Rabbit mAb (CST,

8180), and then the membrane was washed with TBST solution for 3×10 min. The cells were incubated in the dark at room temperature for 2 h with the fluorescent secondary antibody IRDye@680CW Goat (polyclonal) Anti-Rabbit 1gG (H+L), Highly Cross Adsorbed (LI-COR, #926-68071), and then the membrane was washed under the same condition above. Finally, the membrane was detected and imaged on a LI-COR Odyssey Infrared Fluorescence Scanning System, and the results are shown in FIG. 1.

2. Experimental Results

CDK4/6 can make Rb protein lose the arrest on cell cycle by phosphorylating the tumor suppressor protein Rb protein. CDK4/6 inhibitor can prevent the inactivation of tumor suppressor protein Rb and thereby restore the arrest of Rb on cell cycle. It can be seen from FIG. 1 that the compounds 1 and 2 provided by the present disclosure can effectively reduce the phosphorylation of Rb at Ser780 site by acting on MDA-MB-231 breast cancer cells.

Example 7 Pharmacokinetic (PK) Experiment

1. Experimental Method

Male SD rats weighing 300-350 g were fasted overnight prior to the experiment. The compounds to be tested were dissolved in 30% sulfobutyl ether-β-cyclodextrin (SBE-β-CD) and the rats were intragastric administration at 20 mg/kg. The blood was taken from the tails of the rats at 15 min, 30 min, and 1, 2, 3, 4, 6, 8 and 24 hours after administration, with about 0.3 ml of blood at each time point, and then the blood was placed in a centrifuge tube containing K2-EDTA, and centrifuged (2,000 g, 10 min, 4° C.) to take the plasma which was then stored in an ultra-low temperature freezer at −80° C. 50 μL, of plasma sample was mixed with 5 μL of internal standard (IS) and extracted with ethyl acetate. The residue was redissolved in acetonitrile after vacuum drying. The sample was filtered and injected into LC-MS/MS for analysis to determine the concentration of the compounds to be tested.

2. Experimental Results

Figure 2:
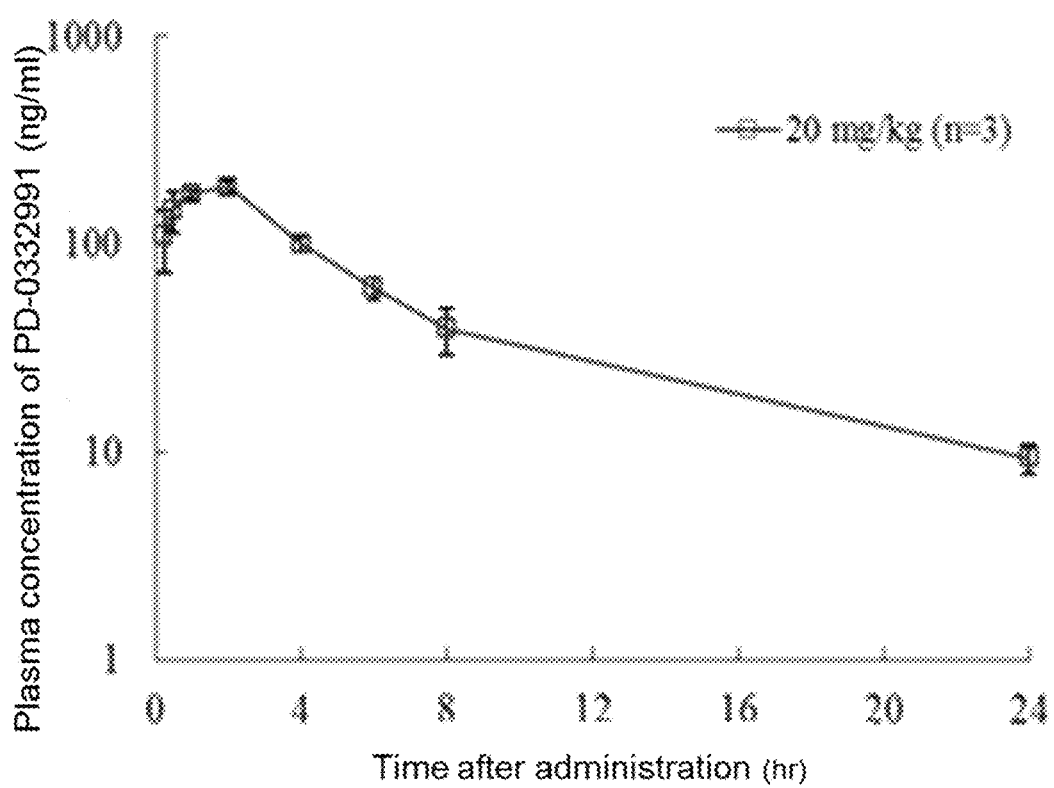
FIG. 2 is a curve of plasma drug concentration of PD-0332991 as a function of time after oral administration to rats in Example 7.
Figure 3:
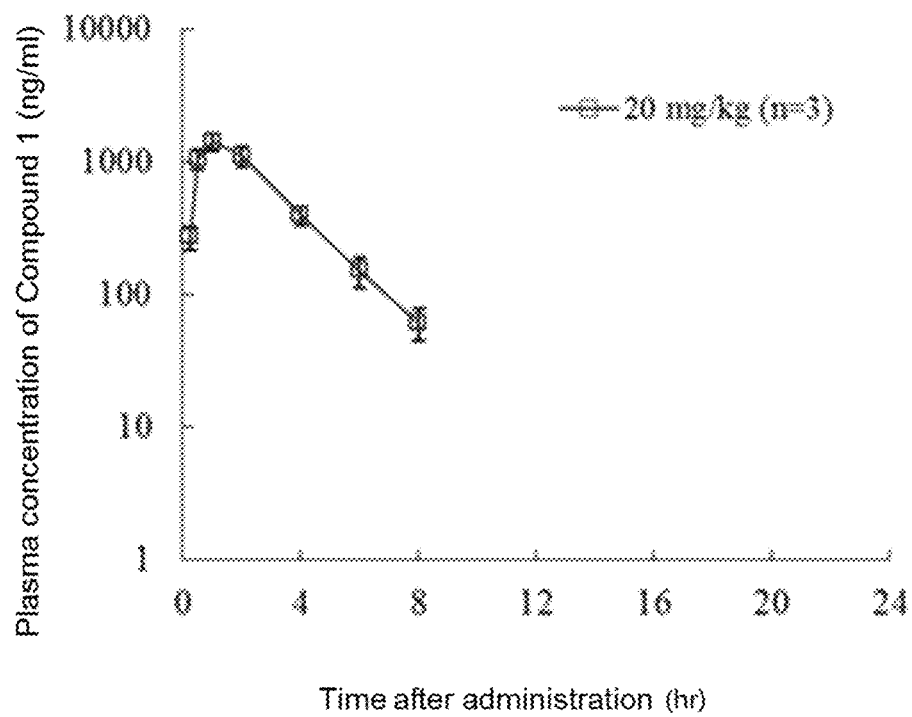
FIG. 3 is a curve of plasma drug concentration of Compound 1 as a function of time after oral administration to rats in Example 7.
Figure 4:
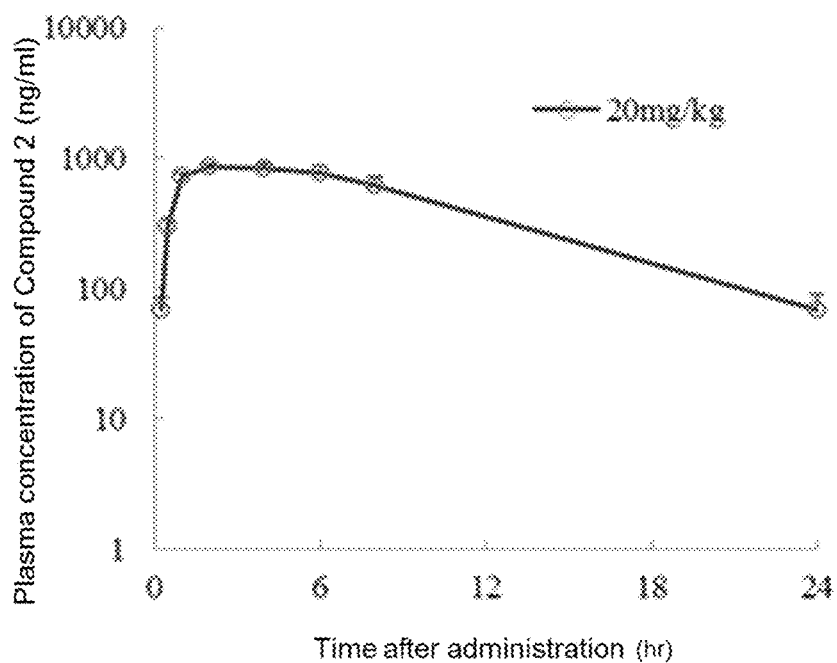
FIG. 4 is a curve of plasma drug concentration of Compound 2 as a function of time after oral administration to rats in Example 7.

The results are shown in the following table and FIGS. 2-4.

TABLE 4

Results of the pharmacokinetic experiment

| Compound | Dosage (mg/kg) | $T_{max}$ (hr) | $C_{max}$ (ng/mL) | $T_{1/2}$ (hr) | $AUC_{last}$ (hr × ng/mL) | $AUC_{inf}$ (hr × ng/mL) |
|---|---|---|---|---|---|---|
| 1 | 20 | 1.5 | 1446.7 | 1.5 | 4402.1 | 4539.6 |
| 2 | 20 | 2.7 | 859.7 | 5.0 | 11197.0 | 11718.0 |
| PD-0332991 | 20 | 1.2 | 212.7 | 10.0 | 1247.7 | 1398.6 |

In the table: $T_{max}$ refers to the peak time, $C_{max}$ refers to the maximum plasma drug concentration, $T_{1/2}$ is the half-life, $AUC_{last}$ refers to the area under the 0-24 hour time-concentration curve, $AUC_{inf}$ refers to the area under the 0-Inf time-concentration curve.

It can be seen from the above results that the compounds 1 and 2 provided by the present disclosure have good absorption and high blood exposure after intragastric administration. Compared to control PD-0332991, the $C_{max}$ of the compounds is about 4-7 times higher and the AUC is about 3-9 times greater. Clinical results of Phase I showed that the blood exposure of palbociclib (PD-0332991) after oral absorption was low, since the elimination half-life was long (Average 25.9 hours), repeated daily dosing would lead to drug accumulation (Keith T, et al. Clin Cancer Res 18:568, 2011). The compounds 1 and 2 were well absorbed orally, the $C_{max}$ and AUC were significantly increased, while the half-lives were relatively short.

Example 8 Pharmacodynamic Experiment

1. Experimental Method

MDA-MB-435 breast cancer cells were obtained from Shanghai Cell Bank of Chinese Academy of Sciences. Cryopreserved cells were thawed in a 37° C. water bath and then placed in RPMI 1640 medium supplemented with 10% fetal bovine serum (FBS), 1% insulin (Bioman Biotech, Shanghai) and incubated in 5% $CO_2$ of Tissue Culture Incubator. The cultured cells were collected when they reached the desired amount, and then washed with serum-free Dulbecco phosphate buffer solution (DPBS). $3.5 \times 10^6$ cells suspended in 0.1 ml of RPMI 1640 and 0.1 ml of ECM gel (Sigma-Aldrich) were injected into the right posterior side subcutaneous area of each mouse with carefully avoiding the blood vessels. The sign of successful transplantation was the formation of a round bulging lump under the skin. Tumor size can be measured approximately two weeks after implantation. The tumor size was measured by a caliper. Tumor volume was calculated by the following formula: tumor volume=(length×width$^2$)/2, change rate of tumor growth (T/C %)=100×ΔT/ΔC.

2. Experimental Results

After 6 days of oral administration of PD-0332991 at 150 mg/kg once daily, the average body weight of the mice was significantly reduced and the dose was subsequently adjusted to 100 mg/kg with oral administration once daily. Compound 1 was orally administered twice daily at 75 mg/kg, and stop the administration of PD-0332991 and Compound 1 after 2 weeks of administration, and continue to observe the tumor size and the change of body weight.

Figure 5:
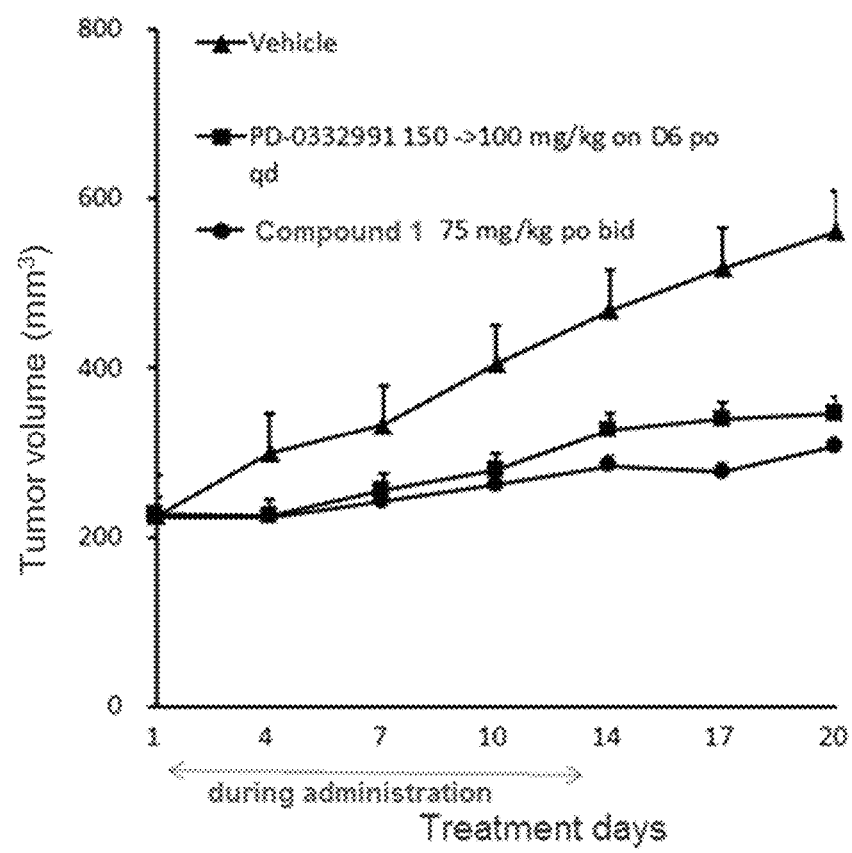
FIG. 5 is a tumor volume change curve of mice after oral administration in Example 8.
Figure 6:
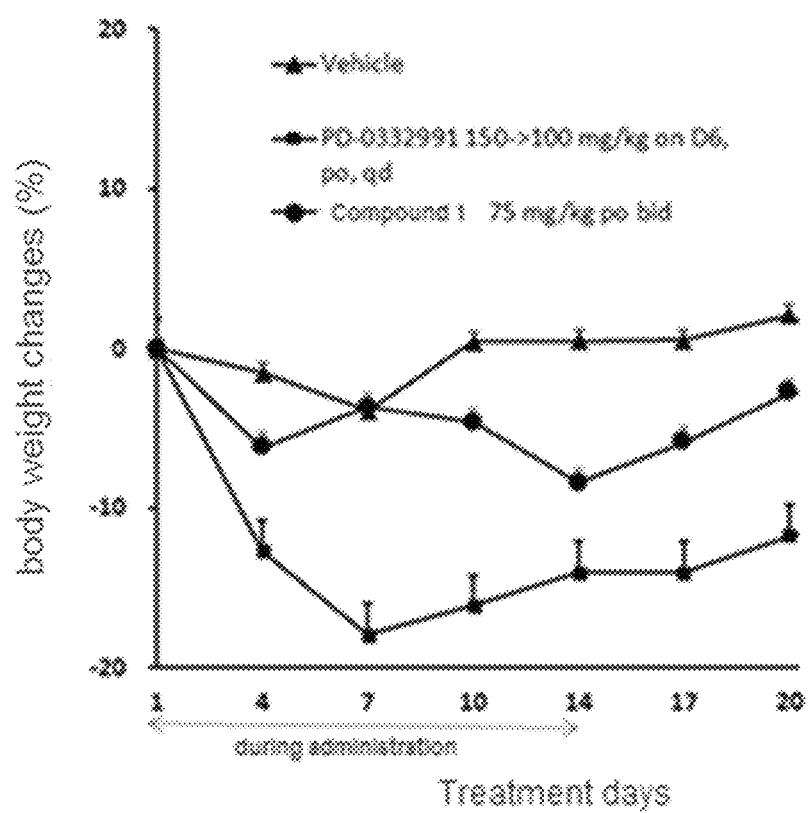
FIG. 6 is a body weight change curve of mice after oral administration in Example 8.

The results are shown in FIG. 5 and FIG. 6, FIG. 5 is a curve of tumor volume change and FIG. 6 is a curve of body weight change of the mice. PD-0332991 and Compound 1 inhibited the tumor growth with the T/C values of 41% and 25%, respectively, after 14 days of administration, which shows that Compound 1 has higher anticancer activity and better safety than PD-0332991. On day 6 after discontinuation (i.e. D20), the T/C values of PD-0332991 and Compound 1 were 35% and 32%, respectively, which shows long effects of the two compounds.

Various technical features of the above embodiments can be combined in any manner. For clarity of description, all possible combinations of various technical features of the above embodiments are not described. However, as long as combinations of these technical features do not contradict with each other, they should be regarded within the scope described in the present specification.

The foregoing examples are merely specific embodiments of the present disclosure, which are described in detail, but they are not intended to limit the protection scope of the present disclosure. It should be noted that any variation or replacement readily figured out by the persons skilled in the art within the technical scope disclosed in the present disclosure shall all fall within the protection scope of the present disclosure. Therefore, the scope of the present disclosure is defined by the appended claims.

What is claimed is:

1. A pyrimidine or pyridopyridone compound or pharmaceutical acceptable salt or stereoisomer thereof as shown in formula (I):

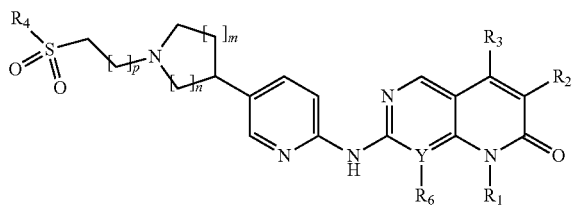

wherein Y is selected from the group consisting of C and N, and no substitution by $R_6$ when Y is N;
$R_1$ is selected from the group consisting of C1-C6 alkyl, C3-C6 cycloalkyl and C3-C6 cycloalkyl-substituted methyl;
$R_2$ is selected from the group consisting of halogen, $COR_5$ and $COOR_5$;
$R_3$ is selected from the group consisting of H and C1-C6 alkyl;
$R_4$ is selected from the group consisting of C1-C6 alkyl, hydroxy-substituted C1-C6 alkyl, alkoxy-substituted C1-C6 alkyl, phenyl and halogen-substituted phenyl;
$R_5$ is selected from the group consisting of H, C1-C6 alkyl, C1-C6 fluoroalkyl and C3-C6 cycloalkyl;
$R_6$ is selected from the group consisting of H, F, CN and $CH_3$;
m is selected from the group consisting of 0, 1 and 2;
n is selected from the group consisting of 1, 2 and 3; and
p is selected from the group consisting of 1, 2 and 3.

2. The pyrimidine or pyridopyridone compound or pharmaceutical acceptable salt or stereoisomer thereof according to claim 1, wherein
$R_4$ is selected from the group consisting of C1-C6 alkyl, hydroxy-substituted C1-C6 alkyl, and alkoxy-substituted C1-C6 alkyl.

3. The pyrimidine or pyridopyridone compound or pharmaceutical acceptable salt or stereoisomer thereof according to claim 2, wherein
$R_4$ is selected from the group consisting of methyl, ethyl, propyl, and isopropyl.

4. The pyrimidine or pyridopyridone compound or pharmaceutical acceptable salt or stereoisomer thereof according to claim 1, wherein
m is 1;
n is 2; and
p is 1 or 2.

5. The pyrimidine or pyridopyridone compound or pharmaceutical acceptable salt or stereoisomer thereof according to claim 1, wherein
Y is N.

6. The pyrimidine or pyridopyridone compound or pharmaceutical acceptable salt or stereoisomer thereof according to claim 1, wherein
$R_1$ is C3-C6 cycloalkyl;
$R_2$ is $COR_5$;
$R_3$ is C1-C6 alkyl;
$R_5$ is C1-C6 alkyl; and
$R_6$ is H.

7. The pyrimidine or pyridopyridone compound or pharmaceutical acceptable salt or stereoisomer thereof according to claim 6, wherein
$R_1$ is cyclopentyl;
$R_2$ is $COR_5$;
$R_3$ is methyl;
$R_5$ is methyl or ethyl; and
$R_6$ is H.

8. The pyrimidine or pyridopyridone compound or pharmaceutical acceptable salt or stereoisomer thereof according to claim 1, wherein the pyrimidine or pyridopyridone compound or pharmaceutical acceptable salt or stereoisomer thereof is a compound selected from the group consisting of:

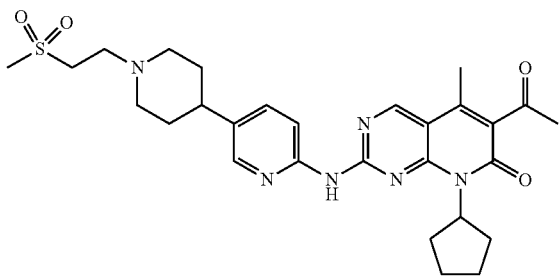

-continued

Compound 6
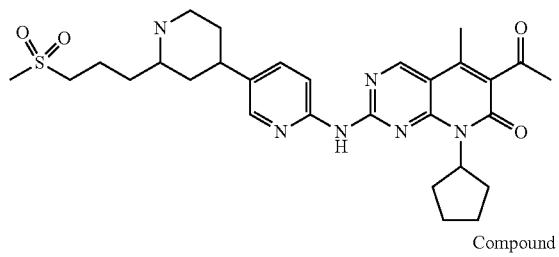

Compound 7
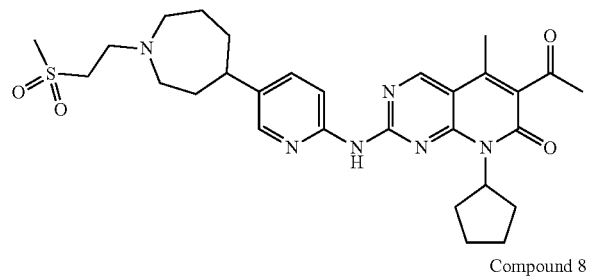

Compound 8
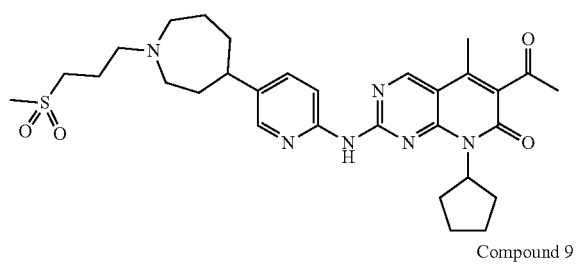

Compound 9
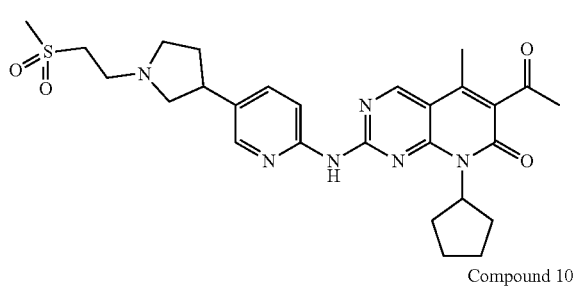

Compound 10
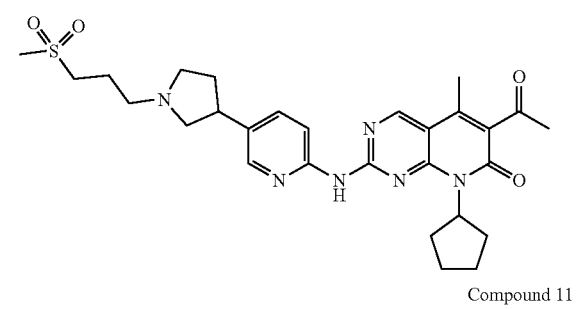

Compound 11

-continued

Compound 12
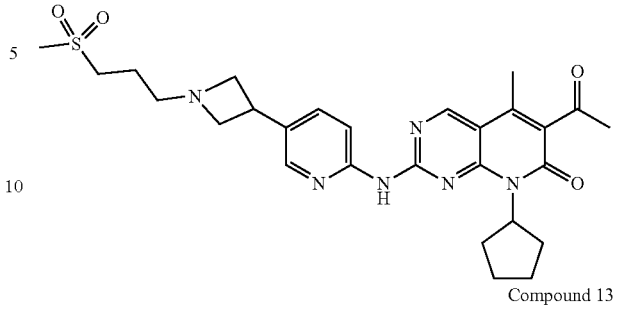

Compound 13
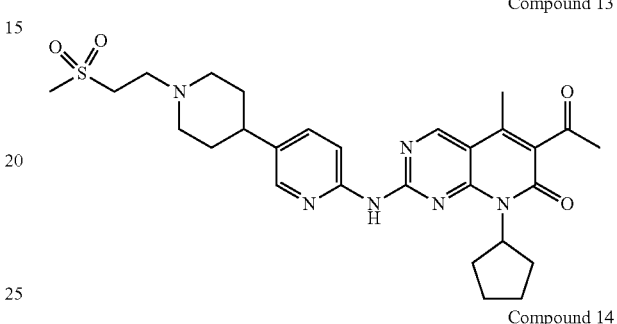

Compound 14
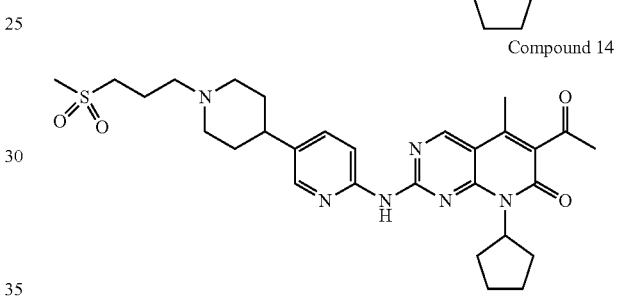

Compound 15
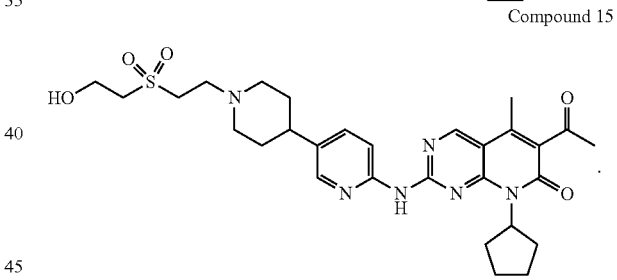

9. A method of treating a cancer, comprising: administrating to a patient in need thereof an antitumor composition comprising the pyrimidine or pyridopyridone compound or pharmaceutical acceptable salt thereof according to claim 1, wherein the cancer is a solid tumor or a haematological tumor.

10. The method of claim 9, wherein the cancer is breast cancer, liposarcoma, non-small cell lung cancer, liver cancer, ovarian cancer, glioblastoma, melanoma, multiple myeloma or mantle cell lymphoma.

11. The method of claim 10, wherein the breast cancer is a locally advanced or metastatic breast cancer with estrogen receptor positive (ER+) and human epidermal growth factor receptor 2 negative(HER$_2$-) in postmenopausal women.

12. An antitumor drug composition, comprising the pyrimidine or pyridopyridone compound or pharmaceutical acceptable salt or stereoisomer thereof according to claim 1 as an active ingredient, and a pharmaceutical acceptable carrier.

* * * * *